US012465233B2

(12) United States Patent
Gaul et al.

(10) Patent No.: US 12,465,233 B2
(45) Date of Patent: Nov. 11, 2025

(54) MULTISTRANDED CONDUCTORS ADAPTED TO DYNAMIC IN VIVO ENVIRONMENTS

(71) Applicant: Foundry Innovation & Research 1, Ltd., Earlsfort Terrace (IE)

(72) Inventors: Robert Gaul, Dublin (IE); Fiachra Sweeney, Dublin (IE); Stephen Sheridan, Dublin (IE); Andrew Hughes, Dublin (IE); James Tucker, Dublin (IE); Sean Quinlan, Dublin (IE)

(73) Assignee: Foundry Innovation & Research 1, Ltd., Dublin (IE)

( * ) Notice: Subject to any disclaimer, the term of this patent is extended or adjusted under 35 U.S.C. 154(b) by 0 days.

(21) Appl. No.: 18/698,255

(22) PCT Filed: Jul. 28, 2023

(86) PCT No.: PCT/IB2023/057703
§ 371 (c)(1),
(2) Date: Apr. 3, 2024

(87) PCT Pub. No.: WO2024/023791
PCT Pub. Date: Feb. 1, 2024

(65) Prior Publication Data

US 2024/0260846 A1 Aug. 8, 2024

Related U.S. Application Data

(60) Provisional application No. 63/393,432, filed on Jul. 29, 2022.

(51) Int. Cl.
*A61B 5/03* (2006.01)

(52) U.S. Cl.
CPC .................................... *A61B 5/036* (2013.01)

(58) Field of Classification Search
CPC .. D02G 3/00; D02G 3/02; D02G 3/38; D02G 3/26; D02G 3/25; D02G 3/28;
(Continued)

(56) References Cited

U.S. PATENT DOCUMENTS 952,161 A * 3/1910 Whyte ..................... D07B 1/06 174/128.1
1,184,912 A * 5/1916 Armitage ................. D02G 3/38 57/210

(Continued)

FOREIGN PATENT DOCUMENTS

AU 2013206194 B2 4/2015
CN 108712880 A 10/2018

(Continued)

OTHER PUBLICATIONS

International Search Report and Written Opinion dated Jan. 3, 2024, in connection with PCT/IB2023/057703, filed Jul. 28, 2023.

(Continued)

*Primary Examiner* — Bao-Thieu L Nguyen
(74) *Attorney, Agent, or Firm* — Downs Rachlin Martin PLLC

(57) ABSTRACT

Multistranded conductors adapted to in vivo environments and methods of making same are disclosed, wherein specific configurations, sequences and directions of wire wraps provide implantable multistranded coils with increased cycle life in in vivo environments as well as desirable electrical performance characteristics.

40 Claims, 4 Drawing Sheets

(58) Field of Classification Search
CPC ........ D02G 3/281; D02G 3/283; D02G 3/285; D02G 3/286; D02G 3/288; D07B 1/04; D07B 1/0626; D07B 1/06; D07B 1/0653; D07B 1/10; D07B 1/0686; D07B 1/068
See application file for complete search history.

(56) References Cited

U.S. PATENT DOCUMENTS 2,133,071 A * 10/1938 Anderson ................ D07B 1/02 57/309
3,209,528 A * 10/1965 Zerr ..................... D07B 1/0686 57/213
3,568,661 A 3/1971 Franklin
3,838,683 A 10/1974 Kolin
4,047,533 A 9/1977 Perciaccante et al.
4,142,412 A 3/1979 McLeod
4,638,252 A 1/1987 Bradshaw
RE32,361 E 2/1987 Duggan
4,733,669 A 3/1988 Segal
4,893,665 A * 1/1990 Reuter ..................... D02G 3/48 57/902
4,926,875 A 5/1990 Rabinovitz et al.
4,947,852 A 8/1990 Nassi et al.
5,127,404 A 7/1992 Wyborny et al.
5,205,292 A 4/1993 Czar et al.
5,316,001 A 5/1994 Ferek-Petric et al.
5,327,713 A * 7/1994 Sakon .................. B60C 9/0007 57/902
5,339,816 A 8/1994 Akamatsu et al.
5,363,848 A 11/1994 Spani et al.
5,476,484 A 12/1995 Hedberg
5,495,852 A 3/1996 Stadler et al.
5,630,836 A 5/1997 Prem et al.
5,687,557 A * 11/1997 De Vos ................ B60C 9/0007 57/200
5,752,522 A 5/1998 Murphy
5,760,341 A * 6/1998 Laske ................. H01B 7/0009 174/128.1
5,852,926 A * 12/1998 Breedlove ............. D07B 1/025 57/200
5,872,520 A 2/1999 Siefert et al.
5,902,308 A 5/1999 Murphy
5,941,198 A * 8/1999 Sullivan .................. D07B 3/12 57/210
5,967,986 A 10/1999 Cimochowski
5,971,933 A 10/1999 Gopakumaran
6,010,511 A 1/2000 Murphy
6,012,457 A 1/2000 Lesh
6,015,386 A 1/2000 Kensey et al.
6,015,387 A 1/2000 Schwartz et al.
6,025,725 A 2/2000 Gershenfeld et al.
6,039,701 A 3/2000 Sliwa et al.
6,053,873 A 4/2000 Govari et al.
6,111,520 A 8/2000 Allen et al.
6,115,633 A 9/2000 Lang et al.
6,115,636 A 9/2000 Ryan
6,164,283 A 12/2000 Lesh
6,206,835 B1 3/2001 Spillman, Jr. et al.
6,231,516 B1 5/2001 Keilman et al.
6,261,233 B1 7/2001 Kantorovich
6,272,830 B1 * 8/2001 Morgan ............... D07B 1/0613 57/902
6,278,379 B1 8/2001 Allen et al.
6,287,253 B1 9/2001 Ortega et al.
6,325,762 B1 12/2001 Tjin
6,339,816 B1 1/2002 Bausch
6,354,999 B1 3/2002 Dgany et al.
6,398,734 B1 6/2002 Cimochowski et al.
6,434,411 B1 8/2002 Duret
6,503,202 B1 1/2003 Hossack et al.
6,574,510 B2 6/2003 Von Arx et al.
6,673,020 B2 1/2004 Okada et al.
6,699,186 B1 3/2004 Wolinsky et al.
6,738,671 B2 5/2004 Christophersom et al.
6,802,811 B1 10/2004 Slepian
6,855,115 B2 2/2005 Fonseca
6,926,670 B2 8/2005 Rich et al.
6,972,553 B2 12/2005 Petrovich et al.
7,065,409 B2 6/2006 Mazar
7,077,812 B2 7/2006 Naghavi
7,082,330 B2 7/2006 Stadler et al.
7,147,604 B1 12/2006 Allen
7,149,587 B2 12/2006 Wardle et al.
7,191,013 B1 3/2007 Miranda et al.
7,225,032 B2 5/2007 Schmeling et al.
7,233,821 B2 6/2007 Hettrick et al.
7,236,821 B2 6/2007 Cates et al.
7,245,117 B1 7/2007 Joy
7,265,676 B2 9/2007 Gordon et al.
7,284,442 B2 10/2007 Fleischman et al.
7,367,984 B2 5/2008 Kulcinski et al.
7,423,496 B2 9/2008 Scheuermann
7,432,723 B2 10/2008 Ellis
7,439,723 B2 10/2008 Allen
7,444,878 B1 11/2008 Pepples
7,452,334 B2 11/2008 Gianchandani et al.
7,454,244 B2 11/2008 Kassab et al.
7,466,120 B2 12/2008 Miller
7,479,112 B2 1/2009 Sweeney et al.
7,481,771 B2 1/2009 Fonseca
7,492,144 B2 2/2009 Powers
7,498,799 B2 3/2009 Allen
7,550,978 B2 6/2009 Joy
7,574,792 B2 8/2009 O'Brien
7,595,647 B2 9/2009 Kroh
7,618,363 B2 11/2009 Yadav
7,621,036 B2 11/2009 Cros
7,621,876 B2 11/2009 Hoctor et al.
7,647,831 B2 1/2010 Corcoran
7,647,836 B2 1/2010 O'Brien
7,662,653 B2 2/2010 O'Brien
7,667,547 B2 2/2010 Ellis
7,677,107 B2 3/2010 Nunez
7,678,135 B2 3/2010 Maahs et al.
7,679,355 B2 3/2010 Allen
7,699,059 B2 4/2010 Fonseca
7,710,103 B2 5/2010 Powers
7,725,160 B2 5/2010 Weber
7,748,277 B2 7/2010 O'Brien
7,778,684 B2 8/2010 Weber et al.
7,786,867 B2 8/2010 Hamel et al.
7,812,416 B2 10/2010 Courcimault
7,829,363 B2 11/2010 You
7,831,301 B2 11/2010 Webb et al.
7,839,153 B2 11/2010 Joy
7,848,813 B2 12/2010 Bergelson et al.
7,854,172 B2 12/2010 O'Brien
7,899,545 B2 3/2011 John
7,908,002 B2 3/2011 Hoijer
7,908,018 B2 3/2011 O'Brien
7,909,770 B2 3/2011 Stern
7,932,732 B2 4/2011 Ellis
7,936,174 B2 5/2011 Ellis
7,955,269 B2 6/2011 Stahmann
7,966,886 B2 6/2011 Corcoran
7,988,719 B2 8/2011 Alt et al.
8,016,766 B2 9/2011 Goedje et al.
8,021,307 B2 9/2011 White
8,025,625 B2 9/2011 Allen
8,026,729 B2 9/2011 Kroh
8,060,214 B2 11/2011 Larson et al.
8,078,274 B2 12/2011 Kassab
8,082,032 B2 12/2011 Kassab et al.
8,099,161 B2 1/2012 Kassab
8,107,248 B2 1/2012 Shin et al.
8,111,150 B2 2/2012 Miller
8,114,143 B2 2/2012 Kassab et al.
8,118,749 B2 2/2012 White
8,154,389 B2 4/2012 Rowland
8,159,348 B2 4/2012 Ellis
8,185,194 B2 5/2012 Kassab
8,209,033 B2 6/2012 Zhang et al.
8,221,405 B2 7/2012 Whisenant et al.

(56) References Cited

U.S. PATENT DOCUMENTS

| | | | |
|---|---|---|---|
| 8,237,451 B2 | | 8/2012 | Joy |
| 8,264,240 B2 | | 9/2012 | Park |
| 8,267,954 B2 | | 9/2012 | Decant, Jr. et al. |
| 8,271,072 B2 | | 9/2012 | Houben et al. |
| 8,278,941 B2 | | 10/2012 | Kroh |
| 8,298,147 B2 | | 10/2012 | Huennekens et al. |
| 8,298,148 B2 | | 10/2012 | Furman |
| 8,353,841 B2 | | 1/2013 | White |
| 8,355,777 B2 | | 1/2013 | White |
| 8,356,399 B2 | | 1/2013 | Kaplan |
| 8,360,984 B2 | | 1/2013 | Yadar |
| 8,374,689 B2 | | 2/2013 | Gopinathan et al. |
| 8,414,495 B2 | | 4/2013 | Halmann |
| 8,432,265 B2 | | 4/2013 | Rowland |
| 8,442,606 B2 | | 5/2013 | Furman |
| 8,442,639 B2 | | 5/2013 | Walker et al. |
| 8,465,436 B2 | | 6/2013 | Griswold |
| 8,465,452 B2 | | 6/2013 | Kassab |
| 8,467,854 B2 | | 6/2013 | Lewis et al. |
| 8,480,594 B2 | | 7/2013 | Eigler et al. |
| 8,493,187 B2 | | 7/2013 | Rowland |
| 8,500,660 B2 | | 8/2013 | Buchwald et al. |
| 8,521,282 B2 | | 8/2013 | Czygan et al. |
| 8,527,046 B2 | | 9/2013 | Connelly et al. |
| 8,556,929 B2 | | 10/2013 | Harper et al. |
| 8,570,186 B2 | | 10/2013 | Nagy |
| 8,600,517 B2 | | 12/2013 | Forsell |
| 8,613,705 B2 | | 12/2013 | Scheurer |
| 8,632,469 B2 | | 1/2014 | Kassab |
| 8,644,941 B2 | | 2/2014 | Rooney et al. |
| 8,665,086 B2 | | 3/2014 | Miner |
| 8,669,770 B2 | | 3/2014 | Cros |
| 8,696,584 B2 | | 4/2014 | Kassab |
| 8,702,613 B2 | | 4/2014 | Kassab |
| 8,706,208 B2 | | 4/2014 | Chiao et al. |
| 8,706,209 B2 | | 4/2014 | Kassab |
| 8,706,219 B2 | | 4/2014 | Feldman |
| 8,728,012 B2 | | 5/2014 | Braido |
| 8,747,313 B2 | | 6/2014 | Tran et al. |
| 8,784,338 B2 | | 7/2014 | Wallace |
| 8,798,712 B2 | | 8/2014 | Gopinathan et al. |
| 8,814,798 B2 | | 8/2014 | Corbucci et al. |
| 8,818,507 B2 | | 8/2014 | Liu et al. |
| 8,825,151 B2 | | 9/2014 | Gopinathan et al. |
| 8,827,904 B2 | | 9/2014 | Ball et al. |
| 8,827,929 B2 | | 9/2014 | O'Dea |
| 8,855,783 B2 | | 10/2014 | Dagan et al. |
| 8,864,666 B2 | | 10/2014 | Kassem |
| 8,870,787 B2 | | 10/2014 | Yadav |
| 8,874,203 B2 | | 10/2014 | Kassab et al. |
| 8,886,301 B2 | | 11/2014 | Kassab |
| 8,894,582 B2 | | 11/2014 | Nunez |
| 8,896,324 B2 | | 11/2014 | Kroh |
| 8,909,351 B2 | | 12/2014 | Dinsmoor et al. |
| 8,918,169 B2 | | 12/2014 | Kassab et al. |
| 8,938,292 B2 | | 1/2015 | Hettrick et al. |
| 8,951,219 B2 | | 2/2015 | Gerber et al. |
| 9,049,995 B2 | | 6/2015 | Blomqvist et al. |
| 9,055,917 B2 | | 6/2015 | Matt et al. |
| 9,060,798 B2 | | 6/2015 | Harper et al. |
| 9,061,099 B2 | | 6/2015 | Gerber et al. |
| 9,066,672 B2 | | 6/2015 | Kassab et al. |
| 9,089,713 B2 | | 7/2015 | John |
| 9,162,065 B2 | | 10/2015 | Karst et al. |
| 9,198,706 B2 | | 12/2015 | Kassab et al. |
| 9,265,428 B2 | | 2/2016 | O'Brien et al. |
| 9,289,132 B2 | | 3/2016 | Ghaffari et al. |
| 9,289,229 B2 | | 3/2016 | Kassab |
| 9,305,456 B2 | | 4/2016 | Rowland |
| 9,314,169 B2 | | 4/2016 | Kassab |
| 9,326,728 B2 | | 5/2016 | Demir et al. |
| 9,332,914 B2 | | 5/2016 | Langston |
| 9,332,916 B2 | | 5/2016 | Kassab |
| 9,333,365 B2 | | 5/2016 | Zhao |
| 9,351,661 B2 | | 5/2016 | Kassab |
| 9,392,940 B2 | | 7/2016 | Snichelotto |
| 9,393,416 B2 | | 7/2016 | Rooney et al. |
| 9,445,743 B2 | | 9/2016 | Kassab |
| 9,489,831 B2 | | 11/2016 | Nagy et al. |
| 9,526,637 B2 | | 12/2016 | Dagan et al. |
| 9,545,263 B2 | | 1/2017 | Lenihan et al. |
| 9,603,533 B2 | | 3/2017 | Lading et al. |
| 9,662,066 B2 | | 5/2017 | Ledet et al. |
| 9,675,257 B2 | | 6/2017 | Kassab |
| 9,675,315 B2 | | 6/2017 | Song et al. |
| 9,713,701 B2 | | 7/2017 | Sarkar et al. |
| RE46,494 E | * | 8/2017 | Bauer ..................... H01F 17/00 |
| 9,717,475 B2 | | 8/2017 | Corl |
| 9,721,463 B2 | | 8/2017 | Rowland |
| 9,724,006 B2 | | 8/2017 | Dumont et al. |
| 9,788,739 B2 | | 10/2017 | John et al. |
| 9,814,395 B2 | | 11/2017 | Stahmann et al. |
| 9,820,673 B2 | | 11/2017 | Feldman |
| 9,872,948 B2 | | 1/2018 | Siess |
| 9,878,080 B2 | | 1/2018 | Kaiser et al. |
| 9,901,722 B2 | | 2/2018 | Nitzan et al. |
| 9,996,712 B2 | | 6/2018 | Sundaram et al. |
| 10,080,528 B2 | | 9/2018 | BeBusschere et al. |
| 10,092,247 B2 | | 10/2018 | Taylor |
| 10,105,103 B2 | | 10/2018 | Goldshtein et al. |
| 10,194,808 B1 | | 2/2019 | Thompson |
| 10,195,441 B2 | | 2/2019 | Kaiser |
| 10,201,285 B2 | | 2/2019 | Sawanoi |
| 10,210,956 B2 | | 2/2019 | Lavi |
| 10,213,129 B2 | | 2/2019 | Kassab |
| 10,219,704 B2 | | 3/2019 | Lavi |
| 10,219,720 B2 | | 3/2019 | Kassab |
| 10,219,724 B2 | | 3/2019 | Stern |
| 10,226,203 B2 | | 3/2019 | Stigall |
| 10,226,218 B2 | | 3/2019 | Rowland |
| 10,231,659 B2 | | 3/2019 | Vanslyke |
| 10,231,701 B2 | | 3/2019 | Ryan |
| 10,236,084 B2 | | 3/2019 | Grady |
| 10,238,311 B2 | | 3/2019 | Kassab |
| 10,238,322 B2 | | 3/2019 | Vanslyke |
| 10,238,323 B2 | | 3/2019 | Vanslyke |
| 10,238,324 B2 | | 3/2019 | Vanslyke |
| 10,240,994 B1 | | 3/2019 | Xu |
| 10,265,024 B2 | | 4/2019 | Lee |
| 10,271,797 B2 | | 4/2019 | Zhang |
| 10,335,042 B2 | | 7/2019 | Schoenie et al. |
| 10,390,714 B2 | | 8/2019 | Wolinsky |
| 10,433,736 B2 | | 10/2019 | Karlovsky et al. |
| 10,537,281 B2 | | 1/2020 | Thompson et al. |
| 10,542,887 B2 | | 1/2020 | Sarkar et al. |
| 10,548,535 B2 | | 2/2020 | Zhang et al. |
| 10,555,704 B2 | | 2/2020 | Averina et al. |
| 10,582,866 B2 | | 3/2020 | Badie et al. |
| 10,588,528 B2 | | 3/2020 | Banet et al. |
| 10,595,734 B2 | | 3/2020 | Thakur et al. |
| 10,596,381 B2 | | 3/2020 | Averina et al. |
| 10,638,980 B2 | | 5/2020 | Gyllensten et al. |
| 10,660,577 B2 | | 5/2020 | Thakur et al. |
| 10,687,715 B2 | | 6/2020 | Jansen et al. |
| 10,702,213 B2 | | 7/2020 | Sharma et al. |
| 10,806,352 B2 | | 10/2020 | Sweeney et al. |
| 10,905,393 B2 | | 2/2021 | Gifford, III et al. |
| 11,006,845 B2 | | 5/2021 | Kuraguntla et al. |
| 11,039,813 B2 | | 6/2021 | Gifford, III et al. |
| 11,206,992 B2 | | 12/2021 | Sweeney et al. |
| 11,272,840 B2 | | 3/2022 | Rothfuss |
| 11,445,924 B2 | | 9/2022 | Joseph |
| 11,452,497 B2 | | 9/2022 | Garza |
| 11,890,082 B2 | | 2/2024 | Cros et al. |
| 2002/0120205 A1 | | 8/2002 | Ferek-Petric |
| 2002/0188207 A1 | | 12/2002 | Richter |
| 2003/0037591 A1 | | 2/2003 | Ashton et al. |
| 2003/0100940 A1 | | 5/2003 | Yodfat |
| 2003/0135971 A1 | | 7/2003 | Liberman |
| 2003/0158584 A1 | | 8/2003 | Cates et al. |
| 2003/0199938 A1 | | 10/2003 | Smits et al. |
| 2004/0106871 A1 | | 6/2004 | Hunyor et al. |
| 2004/0116992 A1 | | 6/2004 | Wardle |
| 2004/0133092 A1 | | 7/2004 | Kain |

(56) References Cited

U.S. PATENT DOCUMENTS

| | | | | |
|---|---|---|---|---|
| 2004/0140939 | A1 | 7/2004 | Haller et al. | |
| 2004/0167596 | A1 | 8/2004 | Richter | |
| 2004/0176672 | A1 | 9/2004 | Silver et al. | |
| 2004/0215235 | A1 | 10/2004 | Jackson et al. | |
| 2005/0049686 | A1 | 3/2005 | Gray et al. | |
| 2005/0049689 | A1 | 3/2005 | Gray et al. | |
| 2005/0137481 | A1 | 6/2005 | Sheard et al. | |
| 2005/0148903 | A1 | 7/2005 | Diamantopoulos | |
| 2005/0149119 | A1* | 7/2005 | Koyfman ................ | A61L 17/12 606/228 |
| 2005/0154321 | A1 | 7/2005 | Wolinsky | |
| 2006/0047327 | A1 | 3/2006 | Colvin et al. | |
| 2006/0056161 | A1 | 3/2006 | Shin | |
| 2006/0079793 | A1 | 4/2006 | Mann et al. | |
| 2006/0100522 | A1 | 5/2006 | Yuan et al. | |
| 2006/0106321 | A1 | 5/2006 | Lewinsky et al. | |
| 2006/0122522 | A1 | 6/2006 | Chavan et al. | |
| 2006/0149166 | A1 | 7/2006 | Zvuloni | |
| 2006/0174712 | A1 | 8/2006 | O'Brien | |
| 2006/0177956 | A1 | 8/2006 | O'Brien | |
| 2006/0178695 | A1 | 8/2006 | Decant | |
| 2006/0207414 | A1* | 9/2006 | Nye ......................... | D04C 1/12 87/7 |
| 2006/0253160 | A1 | 11/2006 | Benditt et al. | |
| 2006/0271119 | A1 | 11/2006 | Ni et al. | |
| 2006/0280351 | A1 | 12/2006 | Luping et al. | |
| 2006/0287602 | A1 | 12/2006 | Obrien et al. | |
| 2006/0287700 | A1 | 12/2006 | White | |
| 2007/0043409 | A1 | 2/2007 | Brian et al. | |
| 2007/0088214 | A1 | 4/2007 | Shuros et al. | |
| 2007/0129637 | A1 | 6/2007 | Wolinsky et al. | |
| 2007/0158769 | A1 | 7/2007 | You | |
| 2007/0199385 | A1 | 8/2007 | O'Brien | |
| 2007/0238998 | A1 | 10/2007 | Nycz et al. | |
| 2007/0249950 | A1 | 10/2007 | Piaget et al. | |
| 2007/0274565 | A1 | 11/2007 | Penner | |
| 2007/0282210 | A1 | 12/2007 | Stern | |
| 2007/0292090 | A1 | 12/2007 | Alphonse et al. | |
| 2008/0015569 | A1 | 1/2008 | Saadat | |
| 2008/0033527 | A1 | 2/2008 | Nunez et al. | |
| 2008/0077016 | A1 | 3/2008 | Sparks | |
| 2008/0097227 | A1 | 4/2008 | Zdeblick et al. | |
| 2008/0177186 | A1 | 7/2008 | Slater et al. | |
| 2008/0275350 | A1 | 11/2008 | Liao | |
| 2008/0287800 | A1 | 11/2008 | Furman | |
| 2008/0294041 | A1 | 11/2008 | Kassab | |
| 2009/0007679 | A1 | 1/2009 | Nunez | |
| 2009/0009332 | A1 | 1/2009 | Nunez | |
| 2009/0011117 | A1 | 1/2009 | Nunez | |
| 2009/0024029 | A1 | 1/2009 | Murashita | |
| 2009/0024042 | A1 | 1/2009 | Nunez | |
| 2009/0024177 | A1 | 1/2009 | Shuros et al. | |
| 2009/0030291 | A1 | 1/2009 | O'Brien | |
| 2009/0036776 | A1 | 2/2009 | Masuda et al. | |
| 2009/0062684 | A1 | 3/2009 | Gregersen et al. | |
| 2009/0105799 | A1 | 4/2009 | Hekmat et al. | |
| 2009/0149766 | A1 | 6/2009 | Shuros et al. | |
| 2009/0177225 | A1 | 7/2009 | Nunez et al. | |
| 2009/0189741 | A1 | 7/2009 | Rowland | |
| 2009/0198293 | A1 | 8/2009 | Cauller | |
| 2009/0270729 | A1 | 10/2009 | Corbucci | |
| 2009/0299427 | A1 | 12/2009 | Liu et al. | |
| 2009/0306507 | A1 | 12/2009 | Hyun et al. | |
| 2010/0056922 | A1 | 3/2010 | Florent | |
| 2010/0063375 | A1 | 3/2010 | Kassab et al. | |
| 2010/0076398 | A1 | 3/2010 | Scheurer et al. | |
| 2010/0076543 | A1 | 3/2010 | Melsheimer et al. | |
| 2010/0094328 | A1 | 4/2010 | O'dea et al. | |
| 2010/0113939 | A1 | 5/2010 | Mashimo et al. | |
| 2010/0121398 | A1 | 5/2010 | Bjorling et al. | |
| 2010/0168577 | A1 | 7/2010 | Vezina | |
| 2010/0222786 | A1 | 9/2010 | Kassab | |
| 2010/0262206 | A1 | 10/2010 | Zdeblick et al. | |
| 2010/0274217 | A1 | 10/2010 | Da Silva et al. | |
| 2010/0324432 | A1 | 12/2010 | Bjorling et al. | |

| | | | | |
|---|---|---|---|---|
| 2011/0105863 | A1 | 5/2011 | Kroh | |
| 2011/0144967 | A1 | 6/2011 | Adirovich | |
| 2011/0160844 | A1 | 6/2011 | Haselby | |
| 2011/0178383 | A1 | 7/2011 | Kassab | |
| 2011/0184301 | A1 | 7/2011 | Holmstrom et al. | |
| 2011/0201990 | A1 | 8/2011 | Franano | |
| 2011/0214898 | A1 | 9/2011 | Huynh | |
| 2011/0265908 | A1 | 11/2011 | Clerc et al. | |
| 2011/0306867 | A1 | 12/2011 | Gopinathan et al. | |
| 2012/0016207 | A1 | 1/2012 | Allen | |
| 2012/0029598 | A1 | 2/2012 | Zhao | |
| 2012/0136385 | A1 | 5/2012 | Cully | |
| 2012/0197118 | A1 | 8/2012 | Lisiecki et al. | |
| 2012/0203090 | A1 | 8/2012 | Min | |
| 2012/0203113 | A1 | 8/2012 | Skerl et al. | |
| 2012/0291788 | A1 | 11/2012 | Griswold et al. | |
| 2012/0296222 | A1 | 11/2012 | Griswold et al. | |
| 2013/0030295 | A1 | 1/2013 | Huennekens et al. | |
| 2013/0041244 | A1 | 2/2013 | Woias et al. | |
| 2013/0041251 | A1 | 2/2013 | Bailey et al. | |
| 2013/0041269 | A1 | 2/2013 | Stahmann et al. | |
| 2013/0060139 | A1 | 3/2013 | Richter | |
| 2013/0073025 | A1 | 3/2013 | Kassab | |
| 2013/0085350 | A1 | 4/2013 | Schugt et al. | |
| 2013/0096409 | A1 | 4/2013 | Hiltner et al. | |
| 2013/0167502 | A1* | 7/2013 | Wilson ..................... | D02G 3/00 264/165 |
| 2013/0178750 | A1 | 7/2013 | Sheehan et al. | |
| 2013/0178751 | A1 | 7/2013 | Min | |
| 2013/0184545 | A1 | 7/2013 | Blomqvist et al. | |
| 2013/0211291 | A1 | 8/2013 | Tran | |
| 2013/0218054 | A1 | 8/2013 | Sverdlik et al. | |
| 2013/0222153 | A1 | 8/2013 | Rowland et al. | |
| 2013/0245469 | A1 | 9/2013 | Yadav | |
| 2013/0245745 | A1 | 9/2013 | Vong et al. | |
| 2013/0261655 | A1 | 10/2013 | Drasler et al. | |
| 2013/0274705 | A1 | 10/2013 | Burnes et al. | |
| 2013/0281800 | A1 | 10/2013 | Saroka et al. | |
| 2013/0296721 | A1 | 11/2013 | Yadav et al. | |
| 2013/0303914 | A1 | 11/2013 | Hiltner et al. | |
| 2013/0303915 | A1 | 11/2013 | Barnard et al. | |
| 2013/0310820 | A1 | 11/2013 | Fernandez et al. | |
| 2013/0317359 | A1 | 11/2013 | Wilson et al. | |
| 2013/0324866 | A1 | 12/2013 | Gladshtein | |
| 2013/0331678 | A1 | 12/2013 | Lading et al. | |
| 2013/0338468 | A1 | 12/2013 | Kassab | |
| 2013/0345650 | A1 | 12/2013 | Amirouche | |
| 2014/0028467 | A1 | 1/2014 | Nagy | |
| 2014/0051965 | A1 | 2/2014 | Zdeblick et al. | |
| 2014/0066738 | A1 | 3/2014 | Kassab | |
| 2014/0073935 | A1 | 3/2014 | Rodriguez-Llorente | |
| 2014/0084943 | A1 | 3/2014 | Kroh | |
| 2014/0088994 | A1 | 3/2014 | Kroh | |
| 2014/0094697 | A1 | 4/2014 | Petroff et al. | |
| 2014/0107768 | A1 | 4/2014 | Venkatasubramanian | |
| 2014/0155710 | A1 | 6/2014 | Rowland | |
| 2014/0155768 | A1 | 6/2014 | Orion et al. | |
| 2014/0155769 | A1 | 6/2014 | White | |
| 2014/0180118 | A1 | 6/2014 | Stigall | |
| 2014/0188011 | A1 | 7/2014 | Wurster et al. | |
| 2014/0200428 | A1 | 7/2014 | Kassab | |
| 2014/0236011 | A1 | 8/2014 | Fan et al. | |
| 2014/0243640 | A1 | 8/2014 | O'Dea | |
| 2014/0266935 | A1 | 9/2014 | Tankiewicz | |
| 2014/0275861 | A1 | 9/2014 | Kroh | |
| 2014/0276011 | A1 | 9/2014 | Schmitt et al. | |
| 2014/0276110 | A1 | 9/2014 | Hoseit | |
| 2014/0276121 | A1 | 9/2014 | Kassab | |
| 2014/0276191 | A1 | 9/2014 | Kassab | |
| 2014/0288085 | A1 | 9/2014 | Yadav | |
| 2014/0288459 | A1 | 9/2014 | Yadav | |
| 2014/0306807 | A1 | 10/2014 | Rowland | |
| 2014/0330143 | A1 | 11/2014 | Kroh et al. | |
| 2014/0350348 | A1 | 11/2014 | Tee et al. | |
| 2014/0371624 | A1 | 12/2014 | Ziaie et al. | |
| 2015/0031966 | A1 | 1/2015 | Ward et al. | |
| 2015/0045649 | A1 | 2/2015 | O'Dea et al. | |
| 2015/0051467 | A1 | 2/2015 | Corbucci et al. | |
| 2015/0065835 | A1 | 3/2015 | Kassab | |

(56) References Cited

U.S. PATENT DOCUMENTS

2015/0065897 A1 3/2015 Bornzin et al.
2015/0088100 A1 3/2015 Oborn
2015/0133796 A1 5/2015 Yadav
2015/0141863 A1 5/2015 Kassab et al.
2015/0157268 A1 6/2015 Winshtein et al.
2015/0208929 A1 7/2015 Rowland
2015/0216425 A1 8/2015 Gladshtein et al.
2015/0223702 A1 8/2015 Vanney et al.
2015/0238121 A1 8/2015 Tu et al.
2015/0257732 A1 9/2015 Ryan
2015/0282720 A1 10/2015 Goldshtein et al.
2015/0282875 A1 10/2015 Harper et al.
2015/0290373 A1 10/2015 Rudser et al.
2015/0297110 A1 10/2015 Kassab
2015/0297111 A1 10/2015 Kassab
2015/0297112 A1 10/2015 Kassab et al.
2015/0297113 A1 10/2015 Kassab
2015/0297818 A1 10/2015 Matsubara et al.
2015/0305808 A1 10/2015 Ku et al.
2015/0313479 A1 11/2015 Stigall et al.
2015/0327786 A1 11/2015 Lading et al.
2016/0000403 A1 1/2016 Vilkomerson
2016/0015507 A1 1/2016 Johnson et al.
2016/0022216 A1 1/2016 Goldshtein et al.
2016/0022447 A1 1/2016 Kim et al.
2016/0029956 A1 2/2016 Rowland
2016/0029995 A1 2/2016 Navratil et al.
2016/0064117 A1* 3/2016 Romero .............. A61M 60/422 174/113 C
2016/0081657 A1 3/2016 Rice
2016/0095535 A1 4/2016 Hettrick et al.
2016/0135787 A1 5/2016 Anderson et al.
2016/0135941 A1 5/2016 Binmoeller et al.
2016/0166232 A1 6/2016 Merritt
2016/0198981 A1 7/2016 Demir et al.
2016/0199204 A1 7/2016 Pung et al.
2016/0210846 A1 7/2016 Rowland et al.
2016/0324443 A1 11/2016 Rowland et al.
2016/0345930 A1 12/2016 Mizukami
2016/0354032 A1 12/2016 Wariar
2016/0374710 A1 12/2016 Sinelnikov et al.
2017/0055048 A1 2/2017 Nagy et al.
2017/0055909 A1 3/2017 Schibli et al.
2017/0065186 A1 3/2017 Joseph et al.
2017/0065824 A1 3/2017 Dagan et al.
2017/0071501 A1 3/2017 Kassab
2017/0127975 A1 5/2017 Bozkurt
2017/0164840 A1 6/2017 Matsumoto
2017/0181677 A1 6/2017 Varsavsky et al.
2017/0211229 A1* 7/2017 Nozaki .................... D07B 1/06
2017/0216508 A1 8/2017 Zilbershlag et al.
2017/0224279 A1 8/2017 Cahan et al.
2017/0232798 A1* 8/2017 Suzuki ................. D07B 1/0613 57/213
2017/0238817 A1 8/2017 Lading
2017/0290686 A1 10/2017 Sirhan et al.
2017/0332945 A1 11/2017 Gopinathan et al.
2017/0340440 A1 11/2017 Ratz
2017/0360312 A1 12/2017 Joseph
2018/0014829 A1 1/2018 Tal et al.
2018/0064931 A1 3/2018 Clements
2018/0092631 A1 4/2018 Liou
2018/0132724 A1 5/2018 Waechter-Stehle et al.
2018/0172785 A1 6/2018 Leussler et al.
2018/0177486 A1 6/2018 Gifford et al.
2018/0220992 A1 8/2018 Gifford et al.
2018/0228951 A1 8/2018 Schwammenthal et al.
2018/0247095 A1 8/2018 Sundaram et al.
2018/0268941 A1 9/2018 Lavi et al.
2018/0269931 A1 9/2018 Hershko et al.
2018/0271371 A1 9/2018 Ziaie et al.
2018/0289488 A1 10/2018 Orth et al.
2018/0289536 A1 10/2018 Burnett
2018/0293409 A1 10/2018 Sundaram et al.
2018/0326151 A1 11/2018 Halpert et al.
2018/0344917 A1 12/2018 Inhaber et al.
2019/0015013 A1 1/2019 Zhu et al.
2019/0029639 A1 1/2019 Gifford et al.
2019/0046047 A1 2/2019 Haase
2019/0053720 A1 2/2019 Sawado
2019/0053767 A1 2/2019 Yamada
2019/0059777 A1 2/2019 Aga et al.
2019/0069784 A1 3/2019 Mukkamala
2019/0069842 A1 3/2019 Rothberg
2019/0069851 A1 3/2019 Sharma
2019/0070348 A1 3/2019 Frost
2019/0076033 A1 3/2019 Sweeney et al.
2019/0082978 A1 3/2019 Van der Horst
2019/0083030 A1 3/2019 Thakur
2019/0090760 A1 3/2019 Kinast
2019/0090763 A1 3/2019 Woerlee
2019/0090856 A1 3/2019 Van der Horst
2019/0099087 A1 4/2019 Cros
2019/0099088 A1 4/2019 Whinnett
2019/0110696 A1 4/2019 Benkowski
2019/0126014 A1 5/2019 Kapur et al.
2019/0150884 A1 5/2019 Maharbiz et al.
2019/0167188 A1 6/2019 Gifford et al.
2019/0175035 A1 6/2019 van der Horst et al.
2019/0358393 A1 11/2019 Marbec
2019/0390403 A1* 12/2019 Waterbury ........... D07B 1/0673
2020/0000364 A1 1/2020 Doodeman et al.
2020/0013510 A1 1/2020 Despenic et al.
2020/0022588 A1 1/2020 Wariar et al.
2020/0022589 A1 1/2020 Banet et al.
2020/0029829 A1 1/2020 Banet et al.
2020/0029857 A1 1/2020 Rowland et al.
2020/0030612 A1 1/2020 Song et al.
2020/0037888 A1 2/2020 Thakur et al.
2020/0037892 A1 2/2020 Banet et al.
2020/0046299 A1 2/2020 An et al.
2020/0069857 A1 3/2020 Schwammenthal et al.
2020/0121187 A1 4/2020 Sarkar et al.
2020/0123703 A1* 4/2020 Smith ....................... B66B 9/00
2020/0129087 A1 4/2020 Sweeney et al.
2020/0131699 A1* 4/2020 Obana ...................... C25D 7/06
2020/0146577 A1 5/2020 Badie et al.
2020/0170515 A1 6/2020 Wen et al.
2020/0170711 A1 6/2020 Hendriks et al.
2020/0187864 A1 6/2020 Sharma
2020/0187865 A1 6/2020 Sharma et al.
2020/0196876 A1 6/2020 Minor et al.
2020/0196899 A1 6/2020 Higgins et al.
2020/0196943 A1 6/2020 Minor et al.
2020/0196944 A1 6/2020 Minor et al.
2020/0196948 A1 6/2020 Cho et al.
2020/0197178 A1 6/2020 Vecchio
2020/0254161 A1 8/2020 Schwammenthal et al.
2020/0345246 A1 11/2020 Hilgers et al.
2021/0038094 A1 2/2021 Sweeney et al.
2021/0060298 A1 3/2021 Arndt et al.
2021/0113099 A1 4/2021 Rogers et al.
2021/0113194 A1 4/2021 Padwal et al.
2021/0177277 A1 6/2021 Cros et al.
2021/0216733 A1 7/2021 Chronos et al.
2021/0244381 A1 8/2021 Sweeney et al.
2021/0254279 A1* 8/2021 Obana .................... B65G 15/36
2021/0401306 A1 12/2021 Sweeney
2022/0071488 A1 3/2022 Andersen et al.
2022/0125312 A1 4/2022 Nazari et al.
2022/0193419 A1 6/2022 Sarkar et al.
2022/0233084 A1 7/2022 Valdez
2022/0240792 A1 8/2022 Wetterling
2022/0265157 A1 8/2022 Charthad
2024/0155147 A1 5/2024 Sun et al.

FOREIGN PATENT DOCUMENTS

CN 110613449 B 5/2020
CN 111867672 A 10/2020
DE 102005035022 A1 11/2006
EP 0399059 A1 5/1989
EP 0538885 A1 4/1993
EP 0897285 A1 2/1999

(56) References Cited

FOREIGN PATENT DOCUMENTS

| | | | |
|---|---|---|---|
| EP | 1162914 | A1 | 12/2001 |
| EP | 1311210 | A2 | 5/2003 |
| EP | 0904009 | B1 | 9/2003 |
| EP | 1545303 | A2 | 6/2005 |
| EP | 1677852 | A2 | 7/2006 |
| EP | 1847217 | A2 | 10/2007 |
| EP | 1851524 | A2 | 11/2007 |
| EP | 1851791 | A2 | 11/2007 |
| EP | 1868496 | A2 | 12/2007 |
| EP | 1871224 | A2 | 1/2008 |
| EP | 1893080 | A2 | 3/2008 |
| EP | 1893081 | A2 | 3/2008 |
| EP | 1893085 | A2 | 3/2008 |
| EP | 2091426 | A2 | 6/2008 |
| EP | 1948007 | | 7/2008 |
| EP | 1993438 | A1 | 11/2008 |
| EP | 2012658 | A2 | 1/2009 |
| EP | 2046242 | A2 | 4/2009 |
| EP | 2117423 | A2 | 11/2009 |
| EP | 2197344 | A1 | 6/2010 |
| EP | 2265164 | A1 | 12/2010 |
| EP | 2021757 | B1 | 4/2011 |
| EP | 2391263 | A2 | 12/2011 |
| EP | 1921983 | B1 | 1/2012 |
| EP | 2060014 | B1 | 1/2012 |
| EP | 1902529 | B1 | 6/2012 |
| EP | 1876945 | B1 | 12/2012 |
| EP | 1928545 | B1 | 1/2013 |
| EP | 2330968 | B1 | 4/2013 |
| EP | 2601633 | A2 | 6/2013 |
| EP | 2449960 | B1 | 10/2013 |
| EP | 2493562 | B1 | 12/2013 |
| EP | 2725969 | A1 | 5/2014 |
| EP | 1993436 | B1 | 6/2014 |
| EP | 3027109 | A1 | 2/2015 |
| EP | 2076170 | B1 | 4/2015 |
| EP | 2895059 | A1 | 7/2015 |
| EP | 2898470 | A1 | 7/2015 |
| EP | 2922465 | A1 | 9/2015 |
| EP | 2317912 | B1 | 11/2015 |
| EP | 1817593 | B1 | 12/2015 |
| EP | 2967432 | A2 | 1/2016 |
| EP | 2268218 | B1 | 2/2016 |
| EP | 2456502 | B1 | 4/2016 |
| EP | 2702578 | B1 | 8/2016 |
| EP | 3057075 | A1 | 8/2016 |
| EP | 2417590 | B1 | 5/2017 |
| EP | 2986252 | B1 | 7/2018 |
| EP | 3359021 | A1 | 8/2018 |
| EP | 3422928 | A1 | 1/2019 |
| EP | 3435847 | A1 | 2/2019 |
| EP | 3435862 | A1 | 2/2019 |
| EP | 3437000 | A1 | 2/2019 |
| EP | 3448330 | A1 | 3/2019 |
| EP | 3448487 | A2 | 3/2019 |
| EP | 3457911 | A1 | 3/2019 |
| EP | 3457924 | A1 | 3/2019 |
| EP | 3457928 | A1 | 3/2019 |
| EP | 3463082 | A1 | 4/2019 |
| EP | 3468462 | A1 | 4/2019 |
| EP | 3591663 | A1 | 1/2020 |
| EP | 3609392 | A1 | 2/2020 |
| EP | 3256043 | B1 | 3/2020 |
| EP | 3629921 | A1 | 4/2020 |
| EP | 3629937 | A1 | 4/2020 |
| EP | 3630275 | A1 | 4/2020 |
| EP | 3634206 | A1 | 4/2020 |
| EP | 3654835 | A1 | 5/2020 |
| EP | 3496808 | B1 | 6/2020 |
| EP | 2654560 | B1 | 7/2020 |
| EP | 3326524 | B1 | 7/2020 |
| EP | 3367884 | B1 | 7/2020 |
| EP | 3678539 | A1 | 7/2020 |
| EP | 3681389 | A1 | 7/2020 |
| EP | 3684260 | A1 | 7/2020 |
| EP | 3684464 | A1 | 7/2020 |
| EP | 3752242 | A1 | 12/2020 |
| EP | 2155307 | B1 | 3/2021 |
| EP | 4039173 | A1 | 8/2022 |
| FR | 3119090 | A1 | 7/2022 |
| GB | 2473529 | A | 3/2011 |
| JP | 2011234884 | A | 11/2011 |
| JP | 4881382 | B2 | 2/2012 |
| JP | 2021513895 | A | 6/2021 |
| JP | 2024516492 | A | 4/2024 |
| KR | 20200123796 | A | 10/2020 |
| WO | 1997042871 | A1 | 11/1997 |
| WO | 1998029030 | A1 | 12/1997 |
| WO | 1998035611 | A1 | 8/1998 |
| WO | 2000055579 | A2 | 9/2000 |
| WO | 2000056210 | A1 | 9/2000 |
| WO | 2001012092 | A1 | 2/2001 |
| WO | 2001013792 | A1 | 3/2001 |
| WO | 2002015823 | A2 | 2/2002 |
| WO | 2002076289 | A2 | 10/2002 |
| WO | 2003061467 | A1 | 7/2003 |
| WO | 2003061504 | A1 | 7/2003 |
| WO | 2003092495 | A1 | 11/2003 |
| WO | 2004073796 | A1 | 9/2004 |
| WO | 2006049796 | A2 | 5/2006 |
| WO | 2006086113 | A2 | 8/2006 |
| WO | 2006086114 | A2 | 8/2006 |
| WO | 2005027998 | A2 | 9/2006 |
| WO | 2006094273 | A2 | 9/2006 |
| WO | 2006096582 | A1 | 9/2006 |
| WO | 2006102905 | A1 | 10/2006 |
| WO | 2006110798 | A2 | 10/2006 |
| WO | 2006025215 | A2 | 11/2006 |
| WO | 2006125215 | A2 | 11/2006 |
| WO | 2007002185 | A2 | 1/2007 |
| WO | 2007002224 | A2 | 1/2007 |
| WO | 2007002225 | A2 | 1/2007 |
| WO | 2007008493 | A1 | 1/2007 |
| WO | 2007028035 | A2 | 3/2007 |
| WO | 2007035332 | A1 | 3/2007 |
| WO | 2007047571 | A2 | 4/2007 |
| WO | 2007047794 | A2 | 4/2007 |
| WO | 2007061841 | A2 | 5/2007 |
| WO | 2007106490 | A2 | 9/2007 |
| WO | 2007106533 | A1 | 9/2007 |
| WO | 2007130628 | A2 | 11/2007 |
| WO | 2008031011 | A1 | 3/2008 |
| WO | 2008031095 | A1 | 3/2008 |
| WO | 2008051907 | A1 | 5/2008 |
| WO | 2008066569 | A2 | 6/2008 |
| WO | 2009006602 | A1 | 1/2009 |
| WO | 2009006608 | A1 | 1/2009 |
| WO | 2009006610 | A1 | 1/2009 |
| WO | 2009006615 | A1 | 1/2009 |
| WO | 2009025648 | A1 | 2/2009 |
| WO | 2009039174 | A1 | 3/2009 |
| WO | 2009111255 | A1 | 9/2009 |
| WO | 2009131879 | A1 | 10/2009 |
| WO | 2011060359 | A2 | 11/2009 |
| WO | 2009146089 | A2 | 12/2009 |
| WO | 2009146090 | A1 | 12/2009 |
| WO | 2009149462 | A2 | 12/2009 |
| WO | 2010011612 | A1 | 1/2010 |
| WO | 2010088279 | A2 | 8/2010 |
| WO | 2010117356 | A1 | 10/2010 |
| WO | 2010117597 | A1 | 10/2010 |
| WO | 2011011104 | A1 | 1/2011 |
| WO | 2012015954 | A1 | 2/2012 |
| WO | 2012015955 | A1 | 2/2012 |
| WO | 2012019191 | A2 | 2/2012 |
| WO | 2012090206 | A2 | 7/2012 |
| WO | 2012140147 | A3 | 10/2012 |
| WO | 2012145187 | A1 | 10/2012 |
| WO | 2012149008 | A2 | 11/2012 |
| WO | 2013003754 | A1 | 1/2013 |
| WO | 2013142387 | A1 | 9/2013 |
| WO | 2013163605 | A1 | 10/2013 |
| WO | 2014006471 | A2 | 1/2014 |
| WO | 2014012670 | A1 | 1/2014 |

(56) References Cited

FOREIGN PATENT DOCUMENTS

| | | | |
|---|---|---|---|
| WO | 2004014456 | A2 | 2/2014 |
| WO | 2014047528 | A1 | 3/2014 |
| WO | 2014054045 | A1 | 4/2014 |
| WO | 2014070316 | A1 | 5/2014 |
| WO | 2014076620 | A2 | 5/2014 |
| WO | 2014081958 | A1 | 5/2014 |
| WO | 2014145531 | A1 | 9/2014 |
| WO | 2014145712 | A1 | 9/2014 |
| WO | 2014162181 | A2 | 10/2014 |
| WO | 2014170771 | A1 | 10/2014 |
| WO | 2014179739 | A1 | 11/2014 |
| WO | 2014197101 | A1 | 12/2014 |
| WO | 2015074018 | A1 | 5/2015 |
| WO | 2015109028 | A1 | 7/2015 |
| WO | 2015157712 | A2 | 10/2015 |
| WO | 2016011309 | A2 | 1/2016 |
| WO | 2016025430 | A1 | 2/2016 |
| WO | 2016131020 | A1 | 8/2016 |
| WO | 2016156446 | A1 | 10/2016 |
| WO | 2016178196 | A2 | 11/2016 |
| WO | 2016178197 | A1 | 11/2016 |
| WO | 2017024051 | A1 | 2/2017 |
| WO | 2017143198 | A1 | 8/2017 |
| WO | 2017198867 | A1 | 11/2017 |
| WO | 2017200956 | A1 | 11/2017 |
| WO | 2017222964 | A1 | 12/2017 |
| WO | 2018013725 | A1 | 1/2018 |
| WO | 2018031714 | A1 | 2/2018 |
| WO | 2018081314 | A1 | 5/2018 |
| WO | 2018102435 | A1 | 6/2018 |
| WO | 2018146690 | A1 | 8/2018 |
| WO | 2018150314 | A1 | 8/2018 |
| WO | 2018156930 | A1 | 8/2018 |
| WO | 2018187582 | A1 | 10/2018 |
| WO | 2018220143 | A1 | 12/2018 |
| WO | 2018220146 | A1 | 12/2018 |
| WO | 2019050831 | A1 | 3/2019 |
| WO | 2019051007 | A1 | 3/2019 |
| WO | 2019051108 | A1 | 3/2019 |
| WO | 2019051007 | A8 | 4/2019 |
| WO | 2019063521 | A1 | 4/2019 |
| WO | 2019079364 | A1 | 4/2019 |
| WO | 2019101855 | A1 | 5/2019 |
| WO | 2019232213 | A1 | 12/2019 |
| WO | 2020023839 | A1 | 1/2020 |
| WO | 2020121221 | A1 | 6/2020 |
| WO | 2020131247 | A1 | 6/2020 |
| WO | 2020132460 | A1 | 6/2020 |
| WO | 2020132668 | A2 | 6/2020 |
| WO | 2020132669 | A1 | 6/2020 |
| WO | 2020132670 | A1 | 6/2020 |
| WO | 2020132671 | A1 | 6/2020 |
| WO | 2020132678 | A1 | 6/2020 |
| WO | 2020144075 | A1 | 7/2020 |
| WO | 2020153765 | A2 | 7/2020 |
| WO | 2021217055 | A1 | 10/2021 |
| WO | 2021236756 | A1 | 11/2021 |
| WO | 2022055920 | A1 | 3/2022 |
| WO | 2022167382 | A1 | 8/2022 |

OTHER PUBLICATIONS

Voroneanu et al., "The relationship between chronic volume overload 3 and elevated blood pressure in hemodialysis patients: 4 use of bioimpedance provides a different perspective 5 from echocardiography and biomarker methodologies," Int Urol Nephrol, Sep. 2010; 42(3):789-97.

Cannesson et al., "Respiratory Variations in Pulse Oximetry Plethysmographic Waveform Amplitude to Predict Fluid Responsiveness in the Operating Room," Anesthesiology 2007; 106:1105-11.

Abraham et al., "The Role of Implantable Hemodynamic Monitors to Manage Heart Failure," Heart Failure Clin 11 (2015) 183-189.

Tallaj et al., "Implantable Hemodynamic Monitors," Cardiol Clin 29 (2011) 289-299.

Tang et al., "Measuring impedance in congestive heart failure: Current options and clinical applications," American Heart Journal 157 (3) 402-411.

Merchant et al., "Implantable Sensors for Heart Failure," Circulation: Arrhythmia and Electrophysiology. 2010; 3: 657-667.

Unadkat, Jignesh V., et al. "The Development of a Wireless Implantable Blood Flow Monitor," Ideas and Innovations, American Society of Plastic Surgeons, 136:199 (2015).

Steinhouse, David et al., "Implant Experience with an Implantable Hemodynamic Monitor for the Management of Symptomatic Heart Failure," PACE (Aug. 2005) vol. 28, pp. 747-753.

Braunschweig, Frieder et al. "Dynamic changes in right ventricular pressures during haemodialysis recorded with an implantable haemodynamic monitor," Nephrol Dial Transplant (2006) 21:176-183.

Karamanoglu, Mustafa et al., "Estimation of cardiac output in patients with congestive heart failure by analysis of right ventricular pressure waveforms," BioMedical Engineering OnLine 2011, 10:36.

Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.

Sharma, Arjun D et al., "Right Ventricular Pressure During Ventricular Arrhythmias in Humans: Potential Implications for Implantable Antitachycardia Devices," JACC vol. 15, No. 3, Mar. 1, 1990, pp. 648-655.

Kjellstrom, Barbo et al., "Changes in Right Ventricular Pressures Between Hemodialysis Sessions Recorded by an Implantable Hemodynamic Monitor," The American Journal of Cardiology, 2009, 103:119-123.

Zile, Michael R. et al., "Transition From Chronic Compensated to Acute Decompensated Heart Failure," Circulation, American Heart Association (2008) 118:1433-1441.

Plicchi, G et al., "Pea I and Pea II Based Implantable Haemodynamic Monitor: Pre Clinical Studies in Sheep," Europace (2002) 4, 49-54.

Vanderheyden, Marc et al., "Continuous Monitoring of Intrathoracic Impedance and Right Ventricular Pressures in Patients With Heart Failure," Circulation Heart Failure (2010) 3:370-377.

Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.

Muller, Laurent et al., "Respiratory variations of inferior vena cava diameter to predict fluid responsiveness in spontaneously breathing patients with acute circulatory failure: need for a cautious use," Critical Care 2012, 16:R188.

Blehar, David J. et al., "Identification of congestive heart failure via respiratory variation of inferior vena cava diameter." American Journal of Emergency Medicine (2009) 27, 71-75.

Miller, Joseph B., et al., "Inferior vena cava assessment in the bedside diagnosis of acute heart failure," American Journal of Emergency Medicine (2012) 30, 778-783.

Corl, Keith et al., "Bedside sonographic measurement of the inferior vena cava caval index is a poor predictor of fluid responsiveness in emergency department patients," Emergency Medicine Australasia (2012) 24, 534-539.

Feissel, et al. "The respiratory variation in inferior vena cava diameter as a guide to fluid therapy," Intensive Care Med (2004) 30: 1834-1837.

Nakao, Shoichiro et al., "Effects of Positional Changes on Inferior Vena Caval Size and Dynamics and Correlations with Right-Sided Cardiac Pressure," American Journal of Cardiology (1987; 59:125-132).

Saha, Narayan M., et al., "Outpatient Use of Focused Cardiac Ultrasound to Assess the Inferior Vena Cava in Patients With Heart Failure," American Journal of Cardiology (2015).

Ishizaki, et al. "Measurement of inferior vena cava diameter for evaluation of venous return in subjects on day 10 of a bed-rest experiment," J Appl Physical 96: 2179-2186, 2004.

(56) References Cited

OTHER PUBLICATIONS

Carbone et al. "Inferior Vena Cava Parameters Predict Re-admission in Ischaemic Heart Failure", European Journal of Clinical Investigations, 2014, 44(4): 341-349.
Bertram, C.D. et al., "Cross-sectional area measurement in collapsed tubes using the transformer principle", Med. & Biol, Eng. & Comput, 1989, 27, 357-364.
Moreno, Augusto et al., "Mechanics of Distension of Dog Veins and Other Very Thin-Walled Tubular Structures", Circulation Research, vol. XXVII, Dec. 1970, pp. 1069-1080.
Tafur, Emilio et al., "Simultaneous Pressure, Flow and Diameter of the Vena Cava with Fright and Exercise", Circulation Research, vol. XIX, Jul. 1966., pp. 42-50.
Guntheroth, Warren G., et al., "Effect of Respiration on Venous Return and Stroke Volume in Cardiac Tamponade", Circulation Research, vol. XX, Apr. 1967, pp. 381-390.
Bartels, Lambertus et al., "Improved Lumen Visualization in Metallic Vascular Implants by Reducing RF Artifacts", Magnetic Resonance in Medicine 47:171-180 (2002).
Guntheroth, Warren G., "in Vivo Measurement of Dimensions of Veins with Implications Regarding Control of Venous Return", IEEE Transactions on Bio-Medical Engineering, Oct. 1969; pp. 247-253.
Kivelitz, Dietmar et al., "A Vascular Stent as an Active Component for Locally Enhanced Magnetic Resonance Imaging", Investigative Radiology, vol. 38, No. 3, 147-152 (2003).
Reddy, Reddy R.V., et al., "A Catheter-Tip Probe for Dynamic Cross-Section Area Measurement", pp. 149-158. (1973).
Stegall, H. Fred, "Survey of Dimension Transducers", Chronically Implanted Cardiovascular Instrumentation, pp. 107-115 (1973).
D. H. Bergel, "The Measurement of Lengths and Dimensions", Cardiovascular Fluid Dynamics, vol. 1. pp. 91-114 (1972).
Baan, Jan et al., "Dynamic Local Distensibility of Living Arteries and its relation to Wave Transmission", Biophysical Journal, vol. 14, (1974); pp. 343-362.
International Search Report and Written Opinion in connection with PCT/US2016/017902, dated Jul. 27, 2016.
Reems, Miryam et al., Central Venous Pressure: Principles, Measurement, and Interpretation, Vetlearn.com, Jan. 2012, Compendium: Continuing Education for Veterinarians, pp. E1-E10.
Yamauchi, Hideko et al., "Correlation Between Blood Volume and Pulmonary Artery Catheter Measurements", Department of Surgery and Surgical Critical Care, University of Hawaii, 2005.
Abraham, William T et al., "Wireless pulmonary artery haemodynamic monitoring in chronic heart failure: a randomised controlled trial"; www.thelancet.com, vol. 377, Feb. 19, 2011, pp. 658-666.
Guiotto, Giovanna et al., "Inferior vena cava collapsibility to guide fluid removal in slow continuous ultrafiltration: a pilot study", Intensive Care Med (2010) 36:696-696.
Martens, Pieter et al., "Current Approach to Decongestive Therapy in Acute Heart Failure", Curr Heart Fail Rep (2015) 12:367-378.
Dupont, Matthias et a., "Impact of Systemic Venous Congestion in Heart Failure", Curr Heart Fail Rep (2011) 8:233-241.
Marik, Paul E. et al., "Hemodynamic parameters to guide fluid therapy", Annals of Intensive Care 2011, 1:1; http://www.annalsofintensivecare.com/content/1/1/1.
Silverberg, Donald et al., "The association between congestive heart failure and chronic renal disease", Curr Opin Nephrol Hypertens 13: 163-170, 2004.
International Search Report and Written Opinion dated Jan. 19, 2021, in connection with PCT/EP2020/079939, filed Oct. 23, 2020.
Lee et al, "Prognostic significance of dilated inferior vena cava in advanced decompensated heart failure" International Journal of Cardiovascular Imaging (2014) 30:1289-1295.
Sonoo T, et. Al., "Prospective analysis of cardiac collapsibility of inferior vena cava using ultrasonography", J Crit Care 2015, http://dx.doi.org/10.1016/j.jcrc.2015.04.124.
Marik, et al., Does Central Venous Pressure Predict Fluid Responsiveness?*: A Systematic Review of the Literature and the Tale of Seven Mares, Chest (2008) 134(1):172-178.
Blehar, et al., Inferior vena cava displacement during respirophasic ultrasound imaging, Critical Ultrasound Journal (2012) 4:18.
Huguet et al., Three-Dimensional Inferior Vena Cava for Assessing Central Venous Pressure in Patients with Cardiogenic Shock, J Am Soc Echocardiogr. 2018; 31: 1034-43 (https://doi.org/10.1016/j.echo.2018.04.003.
Katzarski et al. "A Critical Evaluation of Ultrasound Measurement of Inferior Vena Cava Diameter in Assessing Dry Weight in Normotensive and Hypertensive Hemodialysis Patients," AJKD, vol. 30, No. 4, Oct. 1997, pp. 459-465.
Hellevik et al. Heart Vessels v13, No. 4, p. 175-180, Jul. 1998.
Minten et al. Cardiovasc. Res, vol. 17, No. 10, pp. 627-632, Oct. 1983.
Nippa et al. Journal of Applied Physiology, vol. 30, No. 4, pp. 558-563, Apr. 1971.
Yates PhD dissertation, Stanford CA, SUDAAR 393 1969.
Stergiopulos et al. "Simple and accurate way for estimating total and segmental arterial compliance: The pulse pressure method" Ann Biomed Eng 22, 392-397 (1994).
Reymond et al., Validation of a one-dimensional model of the systemic arterial tree Proceedings of the ASME 2009 Summer Bioengineering Conference (SBC2009); SBC2009-206424.
Rudski et al, Guidelines for the Echocardiographic Assessment of the Right Heart in Adults: A Report from the American Society of Echocardiography (J Am Soc Echocard 2010, 23: 685-713).
Miles et al "Peripheral Intravenous vol. Analysis (PIVA) for Quantitating vol. Overload in Patients Hospitalized With Acute Decompensated Heart Failure—A Pilot Study"; Journal of Cardiac Failure; 2018; https://doi.org/10.1016/j.cardfail.2018.05.003.
Dehkordi et al., Extracting Instantaneous Respiratory Rate From Multiple Photoplethysmogram Respiratory-Induced Variations; Frontiers in Physiology, vol. 9,Article 948; Jul. 18, 2018 (DOI: 10.3389/fphys.2018.00948).
Wang et al., "Internal jugular vein ultrasound for the diagnosis of hypovolemia and hypervolemia in acutely ill adults; a systematic review and meta-analysis"; Internal and Emergency Medicine (2022) 17:1521-1532, Feb. 27, 2022.
Peters et al., "Inductance calculation of planar multi-layer and multi-wire coils: An analytical approach"; Sensors and Actuators A 145-146; pp. 394-404; Nov. 17, 2007.
Extended European Search Report dated Sep. 16, 2020 in connection with EP20178613.4.
International Search Report and Written Opinion dated Mar. 27, 2018, in connection with PCT/US2017/063749.
International Search Report and Written Opinion dated Aug. 29, 2018, in connection with PCT/EP2018/064386.
International Search Report and Written Opinion dated Aug. 21, 2018, in connection with PCT/EP2018/064383.
International Search Report and Written Opinion dated Nov. 4, 2019, in connection with PCT/US2019/034657, filed May 30, 2019.
International Search Report and Written Opinion dated Feb. 27, 2020, in connection with PCT/IB2019/060669 filed Dec. 11, 2019.
International Search Report and Written Opinion dated Mar. 3, 2020, in connection with PCT/US2019/066589 filed Dec. 16, 2019.
Extended European Search Report dated Jul. 3, 2020, in connection with EP20163433.4.
Horizon Scanning Research & Intelligence Centre; Furosemide sc2Wear micro-pump patch for oedema in heart failure; National Institute for Health Research; NIHR HSRIC ID: 11808; Mar. 2016; pp. 1-10; www.hsric.nihr.ac.uk.
ISR Report and Written Opinion dated Dec. 30, 2020, in connection with PCT/EP2020/067713 filed on Jun. 24, 2020.
International Search Report and Written Opinion dated Oct. 19, 2017, in connection with PCT/US2017/046204.
Brennan, J.M., "Handcarried Ultrasound Measurement of the Inferior Vena Cava for Assessment of Intravascular vol. Status in the Outpatient Hemodialysis Clinic"; Clinical Journal of the American Society of Nephrology; pp. 749-753; Jan. 23, 2006.
International Search Report and Written Opinion dated Oct. 20, 2016, in connection with PCT/US2016/045385 filed Aug. 3, 2016.

* cited by examiner

MULTISTRANDED CONDUCTORS ADAPTED TO DYNAMIC IN VIVO ENVIRONMENTS

RELATED APPLICATIONS

The present application claims priority to U.S. Provisional Application No. 63/393,432, filed on Jul. 29, 2022, entitled "Multistranded Conductors Adapted to Dynamic In Vivo Environments", which is incorporated by reference in its entirety herein.

FIELD

The present disclosure generally relates to medical implants and sensors, and more specifically to multistranded conductors adapted to dynamic in vivo environments.

BACKGROUND

Multistranded conductors are utilized in many different applications in many different types of medical devices, in particular for implant applications requiring a high degree of flexibility and resistance to fatigue failure modes. One example is where a control module is connected to an electrode distant to the control module, such as an implanted cardiac pacemaker, defibrillator or in neuromodulation devices. These conductors are exposed to challenging fatigue loading conditions while also requiring superior electrical performance. Another example is as inductive coils utilized in many different types of medical implants, including many types of sensors. One such type of sensor is resonant circuit (RC) based sensors. RC sensors are sensors that deliver a change in resonant frequency as a result of a change in a physical parameter in the surrounding environment. This change causes the resonant frequency produced by the circuit within the device to change. The change in resonant frequency, which may be detected as a "ring-back" signal when the circuit is energized, indicates the sensed parameter or change therein. As is well-known, a basic resonant circuit includes an inductance and a capacitance. In most available RC sensing devices, the change in resonant frequency results from a change in the capacitance of the circuit. For example, plates of a capacitor moving together or apart in response to changes in pressure, thus providing a pressure sensor, is a well-known example of such a device. Less commonly, the change in resonant frequency is based on a change in the inductance of the circuit.

The present Applicant has filed a number of patent applications disclosing new RC monitoring devices using variable inductance for monitoring intravascular dimensions and determining physiological parameters such as patient fluid state based thereon. See, for example, PCT/US17/63749, entitled "Wireless Resonant Circuit and Variable Inductance Vascular Implants for Monitoring Patient Vasculature and Fluid Status and Systems and Methods Employing Same", filed Nov. 29, 2017 (Pub. No. WO2018/102435) and PCT/US19/34657, entitled "Wireless Resonant Circuit and Variable Inductance Vascular Monitoring Implants and Anchoring Structures Therefore", filed May 30, 2019 (Pub. No. WO2019/232213), each of which is incorporated by reference herein, which disclose a number of different embodiments and techniques related to such devices.

Notwithstanding the advances in the art represented by these prior disclosures, improvements in durability, control and signal processing for such implantable multistranded conductors can still be made. In particular, where conductors comprised of very fine wire are subjected to repeated flexing and sharp bends over long periods of implantation, high levels of stress and strain may lead to damage of individual wires, increasing risk of compromised performance or adverse clinical signals caused by increased resistance, a drop in signal strength or increased likelihood of decreasing accuracy in readings produced thereby. In general, long-term durability of multistranded conductors used in medical implants, particularly leads conveying power and data or inductive coils used for sensing modalities, is critical to maintaining device performance in vivo.

The present disclosure thus offers solutions to some unique problems encountered by implanted multistranded conductors as described herein, which have been discovered after introduction and testing of the aforementioned new RC monitoring devices, but which also have broad applicability as conductors for various types of implanted treatment and sensor devices.

SUMMARY

In one implementation, the present disclosure is directed to a multistranded conductor adapted to dynamic in vivo environments. The conductor includes a plurality of wire bundles wrapped together in a wrap direction, wherein: each wire bundle comprises a core bundle with at least one sub-bundle wrapped around each core bundle in the wrap direction; each core bundle comprises at least two core wires wrapped around each other in the wrap direction; each sub-bundle comprises plural first wires wrapped around at least one core wire in the wrap direction; and the first wires and core wires comprise electrically conductive wires each having a wire diameter of less than about 0.003 inches.

In another implementation, the present disclosure is directed to an implantable medical device, which includes a coil formed of a multistranded conductor as disclosed herein, wherein the multistranded conductor has two opposite ends joined with an electrical and mechanical connection.

In yet another implementation, the present disclosure is directed to an implantable sensor, which includes a multistranded conductor formed by wrapping multiple multistranded bundles of individually coated wires, where a direction of twist of the bundles is the same as the direction of the wrapping of the bundles around a central core.

In still yet another implementation, the present disclosure is directed to a method of making a multistranded conductor adapted to dynamic in vivo environments. The method includes forming plural wire sub-bundles by wrapping plural first wires around at least one core wire in a wrap direction; wrapping at least two core wires around themselves in the wrap direction; forming plural core bundles by wrapping plural first wires in the wrap direction around the at least two core wires around themselves; forming plural wire bundles by wrapping plural the sub-bundles in the wrap direction around a core bundle; and wrapping plural the wire bundles around themselves in the wrap direction to form the multistranded conductor.

BRIEF DESCRIPTION OF DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein.

DETAILED DESCRIPTION

Figure 1:
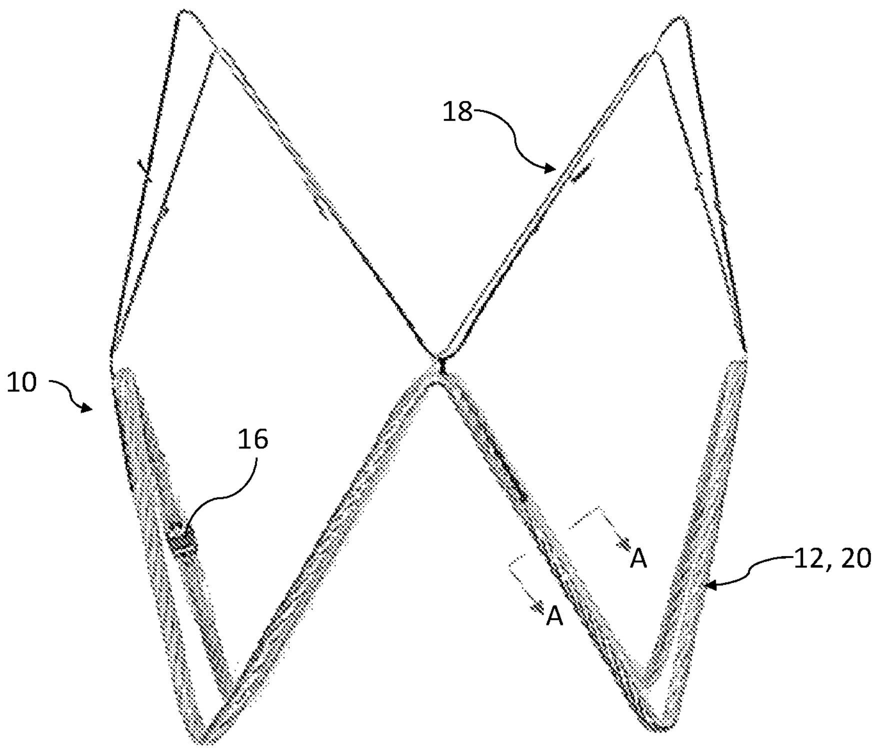
FIG. 1 is a side view of a sensor implant employing a coil in accordance with the present disclosure.

Multistranded conductors used as electrical components in alternating current (AC) radio frequency (RF) applications are frequently constructed with litz wire in order to optimize current flow by reducing skin effect and proximity effect losses. Litz wire is an electrically conductive wire formed from very fine, twisted or braided wires that are each individually insulated. Copper wire is frequently used as the conductor, but in medical implant applications gold wire may be preferred. The thickness of the litz wire is generally selected to be less than the skin effect depth at the anticipated operating frequencies and power. Thus, for use in many medical implant applications, a preferred diameter for individual litz wire may range from less than one thousandth of an inch (<0.001") to a few thousandths of an inch (~0.003").

Such fine wire diameters, combined with the generally overall small size of many medical implants, can make it difficult to include sufficient amount of conductive material in a multistranded conductor to achieve desired electrical performance characteristics while maintaining flexibility or resilience in the conductor. The fine wire may also present an additional challenge in medical implant applications where the wire may be subjected to repeated cycles of bending or shape changes. For example, in vivo conditions may require an implant be capable of withstanding multiple millions of cycles without fatigue failure. While other wire-formed implants, such as stents, vascular filters or components of prosthetic valves, can utilize relatively stiff, strong and thick wire to increase cycle life and avoid fatigue problems, such solutions are not workable for many electrical components utilizing multistranded conductor coils, which are designed to be flexible and/or require fine wire diameters with highly conductive materials such as gold to achieve specific electrical performance criteria.

However, as described further below, the present Applicant unexpectedly discovered that the amount of conductive material can be increased, and fatigue life and fatigue strength improved in small, medically implantable fine litz wire conductors, while improving electrical performance characteristics, by specific twist and wrap directions and order of the litz wire winding during the assembly of the coil. These improvements can be particularly important to maintain high signal fidelity in applications where implanted coils are required to produce signals readable by sensing devices outside of the body.

Disclosed embodiments thus employ a new sequence of forming individual wires into twisted bundles and then further twisting together multiple bundles or wrapping multiple bundles around a central core wherein all twists and wraps are made in the same direction to form a multistranded conductor, which can be formed into an open center coil structure or otherwise used as a highly flexible, fatigue resistant conductor. This new assembly sequence forms a multistranded structure with individual wires laid in the same direction in the bundles as the bundles themselves are laid in the overall conductor structure such that the individual wires are oriented generally transverse with respect to the longitudinal or central axis of the assembled coil. This new assembly sequence is also contrary to the conventional approach to forming multistranded conductors of fine wires, which teaches that alternating twisting/winding directions should be employed to reduce tension in the finished conductor. However, the disclosed new assembly sequence, in addition to providing a relative increase in bending fatigue strength and cycle life as shown and discussed below, facilitates packing of more wire into a similar profile, which can benefit electrical performance characteristics for the coil thus formed.

In a further alternative, the coating of individual litz wires can be selected to improve the durability of the coil by increasing the toughness of the coating and reducing friction between the litz wire interacting with itself and with the supporting frame. Typical examples of coating include PTFE, Polyurethane, nylon, polyimide, polyester or any other applicable polymers. Benefits of coatings can be further increased with multiple layer coatings of different materials to provide different layers of mechanical properties. For example, the elasticity and wear resistance of polyurethane as the base coating may be used with a top layer of PTFE or nylon to reduce friction and/or wear.

For further clarity in describing exemplary embodiments disclosed herein, the following terms are used with the following meanings:

- Winding—refers to the act of creating turns or wraps as defined below.
- Turn(s)—refers to winding individual wires or bundles of wires around the periphery of an open center, which may be circumferentially defined by a frame (except where used in the term "turns per inch" (TPI) which has its conventional meaning in the art).
- Wrap(s)—refers to winding individual wires or bundles of wires around the cross-section of a frame or bundle.
- Twist(s)—refers to "twisting" a group of wires or bundles of wires around themselves by relative counter-rotation of opposite ends of the wires/bundles.
- Bundle/sub-bundle(s)—refers to a group of wires twisted around itself along their length.

Figure 2:
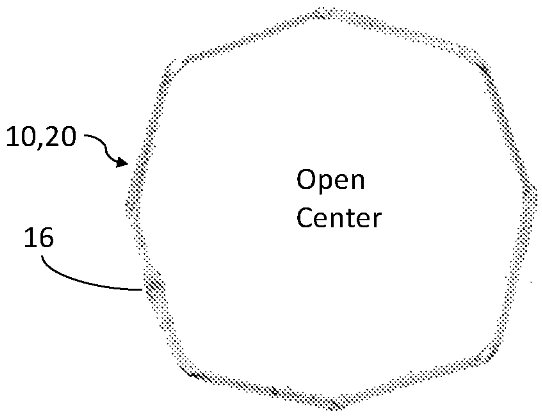
FIG. 2 is a schematic axial view of the sensor implant of FIG. 1 showing the open center configuration.
Figure 3:
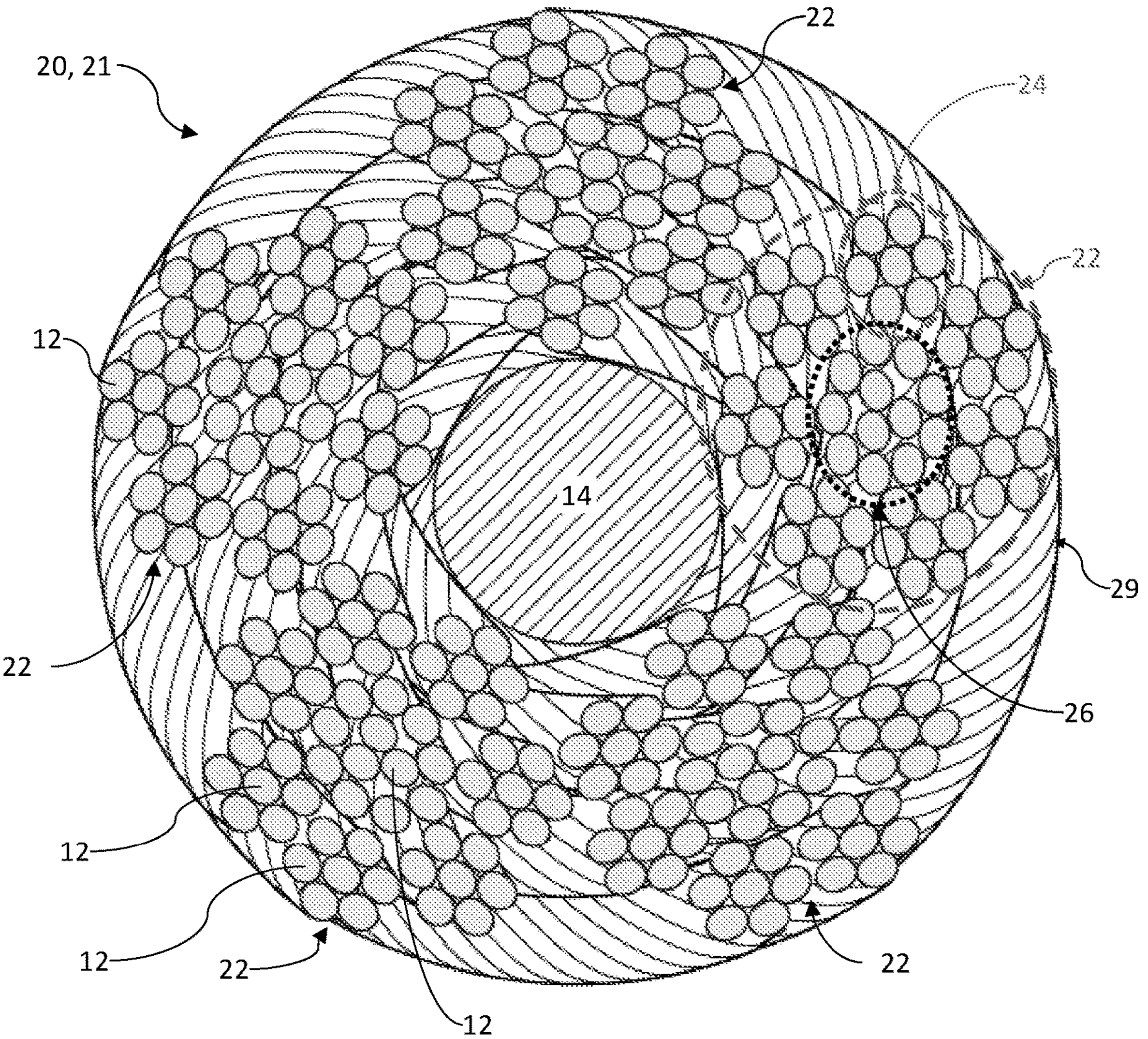
FIG. 3 is a schematic cross-section of a first embodiment of a multistranded conductor according to the present disclosure used to form a coil as in FIG. 1, as seen through section A-A of FIG. 1.
Figure 4:
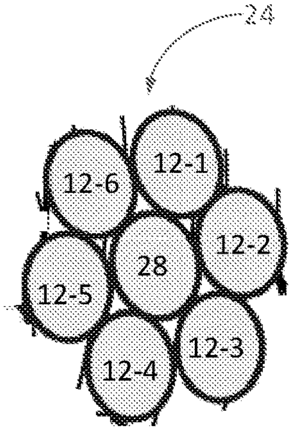
FIG. 4 is a schematic detail view of a cross-section of a portion of FIG. 3 showing a wire sub-bundle according to embodiments of the present disclosure.
Figure 5:
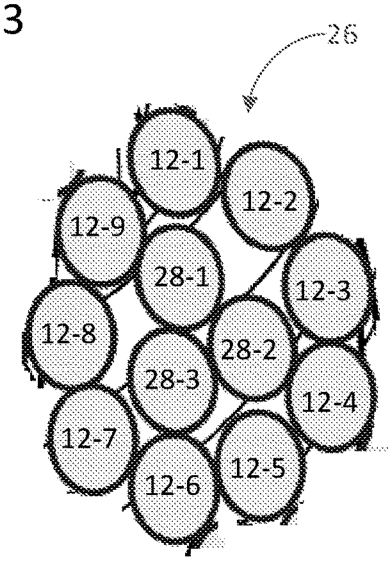
FIG. 5 is another schematic detail view of a cross-section of a portion of FIG. 3 showing a wire core bundle according to embodiments of the present disclosure.

FIGS. 1 and 2 show an example a multistranded conductor used to form the coil 20 of sensor implant 10, in which a plurality of bundles of wires 12 are wrapped multiple times around sensor frame 14 (not visible in FIG. 1, see, e.g., FIGS. 3 and 8) with a single turn around the sensor frame forming an open center coil 20 as described further below. In the illustrated embodiment, sensor 10 also includes a capacitor 16 at which opposite ends of the single turn of wires 12 terminate with an electrical connection to form an RC circuit. In alternative embodiments, plural turns around the open center may be formed, with or without a frame member, with terminal ends of the multistranded conductor forming appropriate electrical connections to an electrical component such as a capacitor or to themselves. Sensor 10 also includes an optional anchor frame 18 in the illustrated device. In addition to details further described below, sensor 10 may include one or more details as described in the aforementioned incorporated applications and patents.

Figure 6:
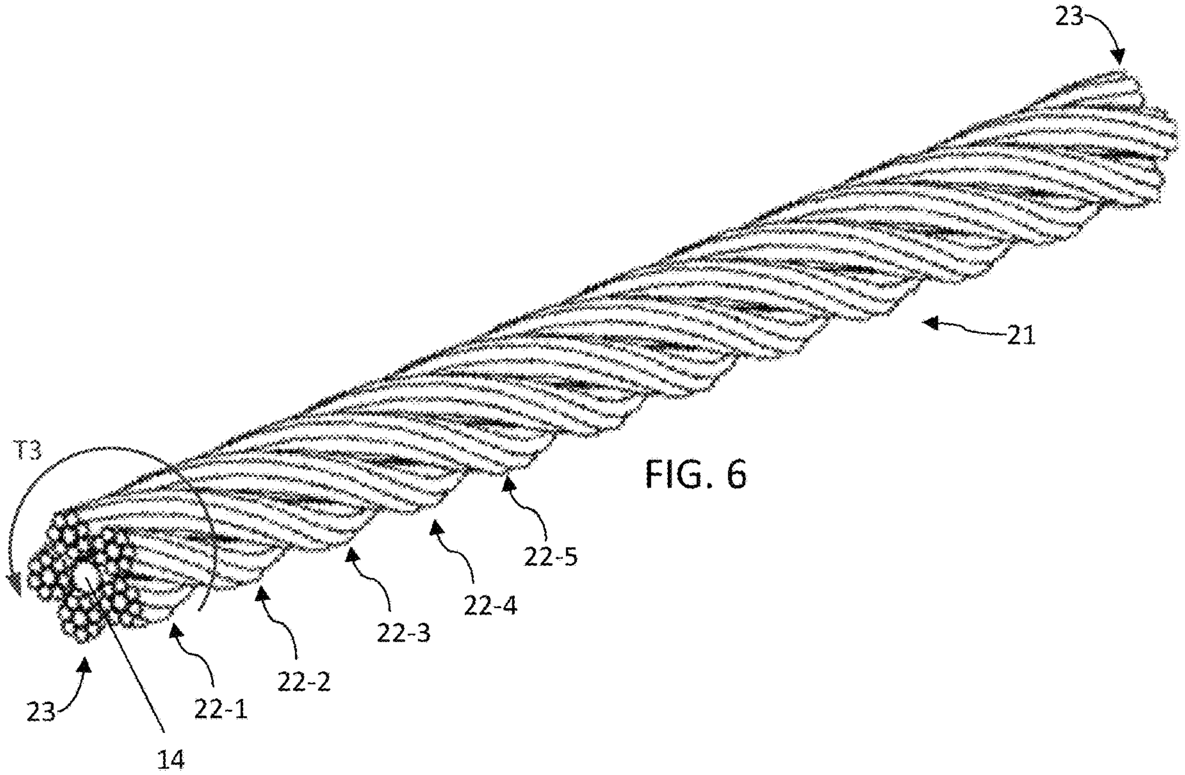
FIG. 6 is a high-level schematic perspective view of a straight section of the multistranded conductor embodiment shown in FIG. 3 (FIG. 6 does not depict individual wires).
Figure 7:
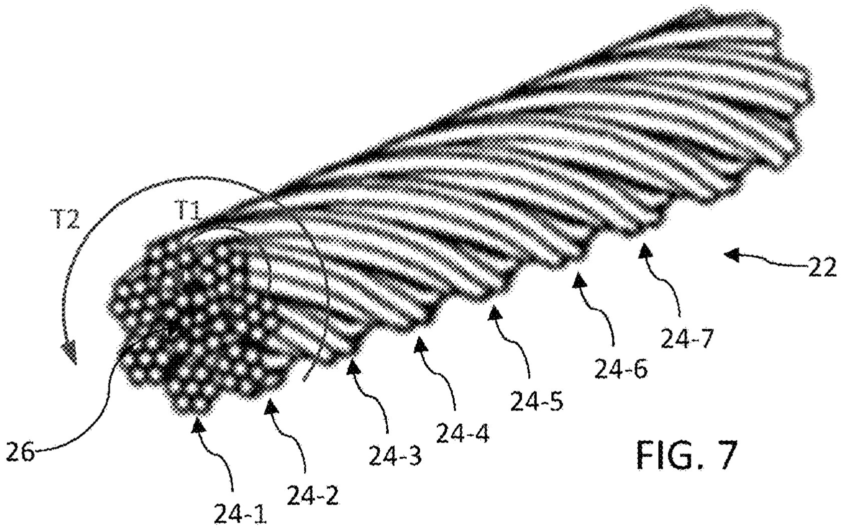
FIG. 7 is an enlarged, detail perspective view of a segment of a wire bundle as utilized in embodiments of multistranded conductors disclosed herein.

In one embodiment, wires 12 are formed into an improved coil 20 by assembling the wires into a section of a multistranded conductor 21 as shown in FIGS. 3-7 and then joining ends 23 (FIG. 6) of multistranded conductor 21 to form open center coil 20. Multistranded conductor 21 comprises five (5) wire bundles 22 wrapped around frame 14 in a wrap direction T3. While a counter-clockwise wrap direction is illustrated in FIGS. 6 and 7, the wrap direction may be either clockwise or counterclockwise as long as the wrap/twist direction is the same for each level of assembly (i.e., direction T1=T2=T3). Each of wire bundles 22 is itself made up of seven (7) sub-bundles 24 comprised of six (6) wires 12 (12-1 through 12-6 in FIG. 4) wrapped around a single core wire 28, also in the same wrap direction (T1). The seven sub-bundles 24 are wrapped around core bundle 26, again in the same wrap direction (T2). Core bundles 26 are comprised of three (3) core wires 28-1, 28-2, 28-3, around which are wrapped nine (9) individual wires 12 (12-1 through 12-9 in FIG. 5), again wrapped in the same wrap direction (T2). In this embodiment, a single turn of open center coil 20 formed from multistranded conductor 21 comprises three-hundred five (305) individual wires 12. Also, this embodiment preferably uses litz wire with a multi-layer nylon over polyurethane coating on each wire 12. It is to be noted that core wires 28 may be the same material and size as all wires 12, or may have different specifications. In the FIG. 3 embodiment as described herein, wires 12 and 28 are the same.

Winding of individual wires and bundles of wires to form the multistranded conductor assembly may be done directly on a sensor frame, such as frame 14, when employed as an open center coil/sensor. Alternatively, they may be wound without a frame for applications such as a pacemaker lead. Once positioned on sensor frame 14, ends 23 of multistranded conductor 21 may be electrically joined to form a single turn, open center coil 20. In the example of sensor 10 in FIG. 1, ends 23 of multistranded conductor 21 are joined to opposite ends of capacitor 16.

In a further alternative embodiment, a sequence of assembly steps for creating a multistranded conductor may be as follows: At the first level, multiple wires are twisted together in a clockwise or counter-clockwise direction to form a sub-bundle. The twists may be made at a specified pitch in turns per inch (TPI), where the pitch is a number selected based on a particular application or use. Thereafter, in a next or second level, multiple sub-bundles as previously formed are twisted together in the same clockwise or counter-clockwise direction to form a bundle of wires. The twists in the bundle may be made at a pitch with the same or different TPI relative to the prior assembly level. In a subsequent or third level, multiple bundles as previously formed are twisted together again in the same clockwise or counter-clockwise twist direction. Again, the pitch of the third level twist may be at the same or different TPI than any prior assembly level as long as the twist direction remains the same. As will be appreciated by persons of ordinary skill, any number of assembly levels may be employed to achieve a specific configuration for a multistranded conductor according to the teachings of the present disclosure. For example, rather than directly twisting wires together at the first level, a first level may comprise first creating a core bundle in which plural wires are twisted around one or more core wires. Where multiple core wires are used, those core wires are twisted in the same direction as the twist at each other assembly level in the multistranded conductor assembly process. Core wires and/or core bundles also may have the same pitch in TPI as any other assembly level. In another example, multiple sub-bundles are twisted around a core bundle, again at the same twist direction but with a common or different TPI pitch. In general, regardless of the number of assembly levels or the pitch at any assembly level, all winding twisting, and wrapping is done in the same direction as described.

Wires 12 used to form multistranded conductors according to the present disclosure may take a variety of forms depending on the intended application for the conductor. For RC sensors using inductive coils as mentioned above, wires 12 may comprise gold litz wire with a diameter in the range of about 0.0010-0.0020 inches, typically about 0.0016 inches (about 0.040 mm). Individual wires also may have single layer or multi-layer coatings to provide electrical insulation and reduce friction between the wire as mentioned. Individual wire coating thickness may be in the range of about 0.000044 to about 0.0002 inches. In one example, a multi-layer coating of nylon over polyurethane has a thickness of about 0.0001 inches (about 0.0025 mm), to provide an overall single litz wire diameter of about 0.0018 inches (about 0.045 mm).

Using the wire sizes of the examples in the preceding paragraph, with a frame 14 having a diameter of approximately 0.011 inches (about 0.285 mm), the three-hundred and five individual wires of multistranded conductor 21 can be configured in an envelope with a nominal total wire diameter of about 0.040 inches (about 1.01 mm). The entire assembly may then be surrounded by an outer coating 29, for example sealed with a heat shrink tubing cover, such as PET heat shrink material. Using an outer coating layer with a thickness of about 0.0004 inches (about 0.01 mm) the nominal diameter of a multistranded conductor with three-hundred five wires may be only about 0.0476 inches (about 1.2084 mm).

Figure 8:
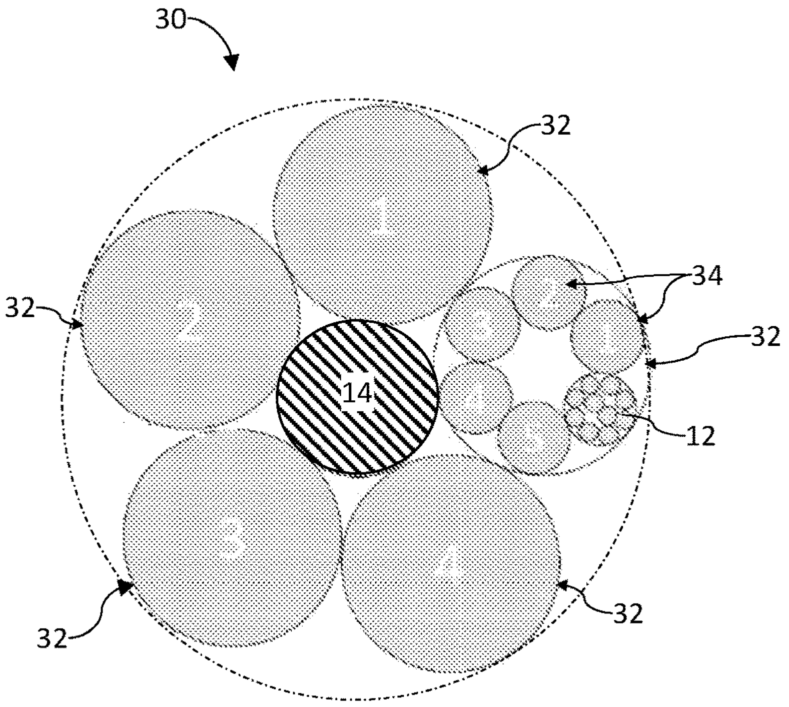
FIG. 8 is a schematic cross-section of an alternative embodiment of a multistranded conductor according to the present disclosure, which may be used to form a coil as in FIG. 1, again as seen through section A-A of FIG. 1.

In an earlier alternative embodiment, as shown in FIG. 8, multistranded conductor 30 comprises five (5) bundles 32 wrapped around frame 14. Each of bundles 32 is formed of six (6) sub-bundles 34 twisted around one another. Each of sub-bundles 34 comprises ten (10) individual wires 12 twisted together. Multistranded conductor 30 was formed in accordance with more conventional techniques, meaning that each successive wrapping/twisting pass was made in the opposite rotational direction from the prior pass. Using this configuration, also with a frame diameter of 0.011 inches (about 0.285 mm), multistranded conductor 30 provided a single turn coil for sensor 10 with three-hundred (300) individual wires 12 within a nominal total coated envelope diameter of 0.046 inches (about 1.17 mm).

Figure 9:
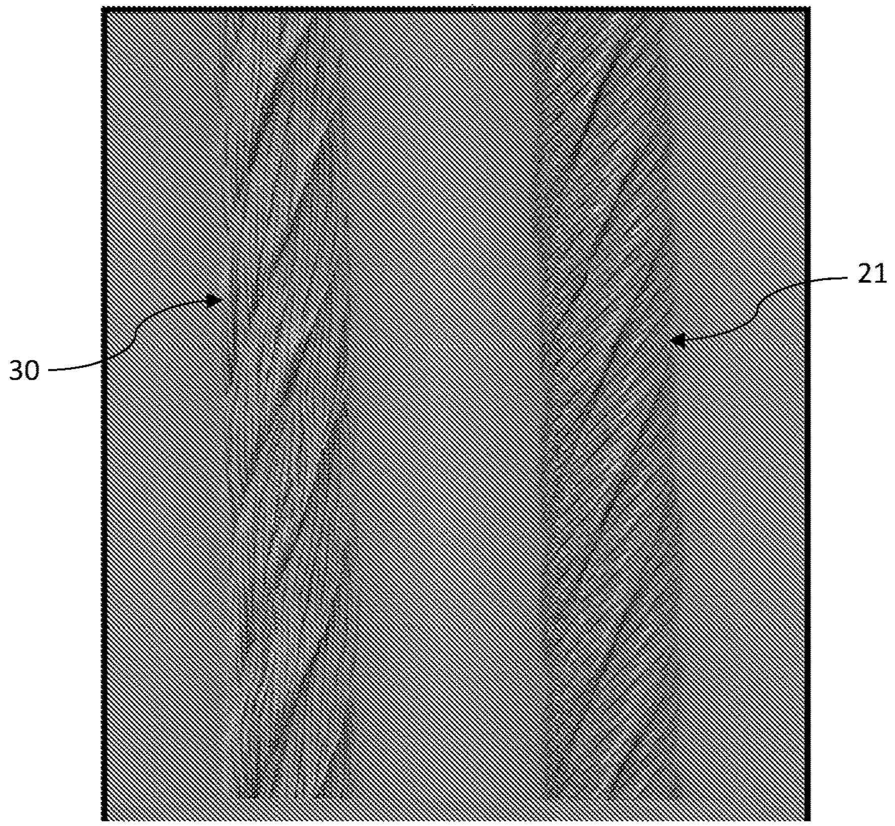
FIG. 9 is a photograph showing a portion of the multistranded conductor embodiments shown in FIGS. 3 and 8, respectively.

FIG. 9 shows a side-by-side comparison of multistranded conductors 21 and 30. The change made between multistranded conductor 30 and multistranded conductor 21 provided a number of unexpected advantages in multistranded conductor 21 when employed to form coils as used in sensor 10. As detailed in Tables 1 and 2 below, these advantages include a greater wire density within approximately the same cross-sectional envelope, improved deflection and fatigue cycle performance, and improved electrical performance. For example, as shown in Table 1, wire density, calculated as the ratio of area occupied by wire to the total cross-sectional area of the nominal multistranded conductor envelope increased to over 40%.

TABLE 1

| Wire Density Comparison | |
|---|---|
| | Wire Density as % of area |
| Coil using conductor 30 | 35.1% |
| Coil using conductor 21 | 47.8%% |

The change in wire configuration also provided a substantial increase in coil signal quality, measured as Q factor. To assess relative Q factors of sensors 10 using coils made with multistranded conductor 21 and 30 configurations, readings were taken using two sensors 10, each constructed using the different multistranded conductor embodiments. Readings of the peak energy stored in the circuit are measured via the length of the ringdown or oscillation of the received signal for each sensor type. This measurement relates to the quality factor or Q factor of the signal. As reflected in Table 2 below, the sensor coil using multistranded conductor 21 provided a more than 15% increase in Q factor.

TABLE 2

| Electrical Performance Comparison Average Q factor (signal quality) | | | |
|---|---|---|---|
| Conductor 30 coil | Conductor 21 coil | Difference | % Increase |
| 40.9276 | 48.5899 | 7.6623 | 18.721596 |

Coils formed from multistranded conductor 21 also provided a substantial increase in fatigue performance compared to coils made using multistranded conductor 30. In fatigue testing, with both types of coils subjected to the same defection and cycle conditions, the coil made from multistranded conductor 21 showed an increase in fatigue performance of over 5000% (50 times+) relative to the coil made with multistranded conductor 30.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure or of the inventions as set forth in following claims.

What is claimed is:

1. A multistranded conductor adapted to dynamic in vivo environments, comprising a plurality of wire bundles wrapped together in a wrap direction, wherein:

each wire bundle comprises a core bundle with at least one sub-bundle wrapped around each core bundle in said wrap direction;

each core bundle comprises at least two core wires wrapped around each other in said wrap direction;

each sub-bundle comprises plural first wires wrapped around at least one core wire in said wrap direction; and said first wires and core wires comprise electrically conductive wires each having a wire diameter of less than about 0.003 inches.

2. The multistranded conductor of claim 1, further comprising a central frame member with said wire bundles wrapped together in said wrap direction around the central frame member.

3. The multistranded conductor of claim 1, wherein said first wires and core wires have diameters in a range of about 0.001 to about 0.002 inches.

4. The multistranded conductor of claim 3, wherein all said core wires and first wires are substantially the same diameter.

5. The multistranded conductor of claim 1, comprising three to six wire bundles.

6. The multistranded conductor of claim 5, wherein the number of wire bundles is five.

7. The multistranded conductor of claim 5, comprising four to eight sub-bundles wrapped around each core bundle.

8. The multistranded conductor of claim 7, wherein the number of sub-bundles wrapped around each core bundle is seven.

9. The multistranded conductor of claim 7, comprising up to five core wires in each core bundle.

10. The multistranded conductor of claim 9, wherein the number of core wires in each core bundle is three.

11. The multistranded conductor of claim 9, wherein each sub-bundle comprises four to seven first wires wrapped around said at least one core wire.

12. The multistranded conductor of claim 11, wherein each sub-bundle has six first wires wrapped around one core wire.

13. The multistranded conductor of claim 1, wherein said first wires and core wires comprise gold wire.

14. The multistranded conductor of claim 1, wherein each of said first wires and core wires are individually coated with a friction-reducing coating.

15. The multistranded conductor of claim 14, wherein said coating comprises two layers of dissimilar material.

16. The multistranded conductor of claim 15, wherein said coating comprises a top layer of PTFE (Polytetrafluoroethylene) or nylon over a layer of polyurethane directly on the wires.

17. The multistranded conductor of claim 1, further comprising an outer layer of heat shrink tubing over all said wires.

18. An implantable medical device, comprising a coil formed of a multistranded conductor according to claim 1, wherein the multistranded conductor has two opposite ends joined together with an electrical and mechanical connection.

19. An implantable medical device, comprising a coil formed of a multistranded conductor comprising a plurality of wire bundles wrapped together in a wrap direction, wherein each wire bundle comprises a core bundle with at least one sub-bundle wrapped around each core bundle in said wrap direction, each core bundle comprises at least two core wires wrapped around each other in said wrap direction, each sub-bundle comprises plural first wires wrapped around at least one core wire in said wrap direction, and said first wires and core wires comprise electrically conductive wires each having a wire diameter of less than about 0.003 inches, and wherein the multistranded conductor has two opposite ends joined together with an electrical and mechanical connection, and a capacitor is disposed between and electrically joined to said two opposite conductor ends.

20. The medical device of claim 18, wherein said coil is formed with one or more turns of the multistranded conductor around an open center.

21. The medical device of claim 20, wherein said coil is wrapped around a frame member.

22. A method of making a multistranded conductor adapted to dynamic in vivo environments, comprising:

- forming plural wire sub-bundles by wrapping plural first wires around at least one core wire in a wrap direction;
- wrapping at least two core wires around themselves in said wrap direction;
- forming plural core bundles by wrapping plural first wires in said wrap direction around said at least two core wires around themselves;
- forming plural wire bundles by wrapping plural said sub-bundles in said wrap direction around a core bundle; and
- wrapping plural said wire bundles around themselves in said wrap direction to form the multistranded conductor.

23. The method of claim 22, further comprising wrapping said plural wire bundles around themselves on a central frame member.

24. The method of claim 22, further comprising individually coating said first wires and said core wires with a friction-reducing coating before said wrapping and forming steps.

25. The method of claim 24, wherein said coating comprises an outer layer of PTFE (Polytetrafluoroethylene) or nylon over a layer of polyurethane directly on the wires.

26. The method of claim 22, wherein said wrapping plural said wire bundles comprises wrapping three to six wire bundles.

27. The method of claim 26, wherein the number of wire bundles is five.

28. The method of claim 22, wherein said forming plural sub-bundles comprises wrapping four to seven first wires around said at least one core wire.

29. The method of claim 28, wherein each sub-bundle has six first wires wrapped around one core wire.

30. The method of claim 22, wherein said forming plural wire bundles comprises wrapping four to eight sub-bundles around each core bundle.

31. The method of claim 30, wherein the number of sub-bundles wrapped around each core bundle is seven.

32. The method of claim 22, wherein said forming plural core bundles comprises wrapping up to five core wires in each core bundle.

33. The method of claim 32, wherein the number of core wires in each core bundle is three.

34. The multistranded conductor of claim 1, wherein the multistranded conductor comprises at least 305 individual first wires and core wires and has an overall wire diameter of not greater than 0.04 inches.

35. The medical device of claim 18, wherein the multistranded conductor comprises at least 305 individual first wires and core wires and has an overall wire diameter of not greater than 0.04 inches.

36. The method of claim 22, wherein the multistranded conductor comprises at least 305 individual first wires and core wires and has an overall wire diameter of not greater than 0.04 inches.

37. The multistranded conductor of claim 1, wherein said wrap direction is one of a clockwise direction or a counterclockwise direction.

38. The method of claim 22, wherein said wrap direction is one of a clockwise direction or a counterclockwise direction.

39. The multistranded conductor of claim 1, wherein each core bundle comprises nine wires wrapped in the wrap direction around the core wires.

40. The multistranded conductor of claim 10, wherein each core bundle comprises nine wires wrapped in the wrap direction around the three core wires.

* * * * *